US009791403B2

(12) United States Patent
Mickelson et al.

(10) Patent No.: US 9,791,403 B2
(45) Date of Patent: Oct. 17, 2017

(54) NANOPARTICLE-BASED GAS SENSORS AND METHODS OF USING THE SAME

(71) Applicant: The Regents of the University of California, Oakland, CA (US)

(72) Inventors: William Mickelson, San Francisco, CA (US); Alex Zettl, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 749 days.

(21) Appl. No.: 14/045,711

(22) Filed: Oct. 3, 2013

(65) Prior Publication Data

US 2014/0138259 A1 May 22, 2014

Related U.S. Application Data

(60) Provisional application No. 61/710,488, filed on Oct. 5, 2012.

(51) Int. Cl.
*G01N 27/403* (2006.01)
*G01N 33/00* (2006.01)
*G01N 27/12* (2006.01)

(52) U.S. Cl.
CPC ......... *G01N 27/403* (2013.01); *G01N 27/127* (2013.01); *G01N 33/0044* (2013.01)

(58) Field of Classification Search
CPC ......... G01N 27/407; G01N 27/4073–27/4076; G01N 27/4141; G01N 27/4162; G01N 33/0004; G01N 33/0027; G01N 33/0036–33/0057; F01N 2560/02–2560/027
See application file for complete search history.

(56) References Cited

U.S. PATENT DOCUMENTS

| 4,432,224 A | * | 2/1984 | Typpo | G01N 33/0044 73/24.01 |
| 5,356,756 A | | 10/1994 | Cavicchi et al. | |
| 7,441,440 B2 | | 10/2008 | Sberveglieri et al. | |
| 8,201,992 B2 | | 6/2012 | Horovitz et al. | |
| 2003/0099575 A1 | * | 5/2003 | Sung et al. | G01N 27/12 422/88 |
| 2004/0009605 A1 | | 1/2004 | Brown et al. | |

FOREIGN PATENT DOCUMENTS

| EP | 1273908 A1 * | 1/2003 | ............. G01N 27/12 |
| WO | WO 01/02844 A1 * | 1/2001 | ............. G01N 27/12 |

OTHER PUBLICATIONS

EPO computer-generated English language translation of the Description section of Alepee et al. EP 1273908 A1 downloaded from the EPO webstie on May 26, 2016.*

(Continued)

*Primary Examiner* — Alexander Noguerola
(74) *Attorney, Agent, or Firm* — Rudy J. Ng; Bret E. Field; Bozicevic, Field & Francis LLP

(57) ABSTRACT

Gas sensors are provided. The gas sensors include a gas sensing element having metal oxide nanoparticles and a thin-film heating element. Systems that include the gas sensors, as well as methods of using the gas sensors, are also provided. Embodiments of the present disclosure find use in a variety of different applications, including detecting whether an analyte is present in a gaseous sample.

22 Claims, 14 Drawing Sheets

(56) References Cited

OTHER PUBLICATIONS

EPO computer generated English language translation of the Description section of Chaudret et al. WO 01/02844 A1 downloaded from the EPO webstie on May 26, 2016.*
Bhat et al. "Integrated CMOS Gas Sensors," 2009 2nd International Workshop in Electron Devices and Semiconductor Technology.*
Geist et al. "Simple Thermal-Efficiency Model for CMOS-Microhotplate Design, Journal of Research of the National Institute of Standards and Technology," vol. 111, No. 3, May-Jun. 2006.*
Afridi et al., "A Monolithic CMOS Microhotplate-Based Gas Sensor System", IEEE Sensors Journal, Dec. 2002, 644-655, vol. 2, No. 6.
Comini et al., "Metal oxide nano-crystals for gas sensing", Analytica Chimica Acta, May 2006, 28-40, vol. 568, Issues 1-2.
Rout et al, "H2S sensors based on tungsten oxide nanostructures", Sensors and Actuators B, Jan. 2008, 488-493, vol. 128, Issue 2.

\* cited by examiner

NANOPARTICLE-BASED GAS SENSORS AND METHODS OF USING THE SAME

CROSS-REFERENCE TO RELATED APPLICATION

Pursuant to 35 U.S.C. §119 (e), this application claims priority to the filing date of U.S. Provisional Patent Application Ser. No. 61/710,488 filed on Oct. 5, 2012, the disclosure of which is herein incorporated by reference.

STATEMENT REGARDING FEDERALLY SPONSORED RESEARCH

This invention was made with government support under Grant No. EEC-0832819 awarded by the National Science Foundation, and under Grant No. DE-AC02-05CH11231, awarded by the Department of Energy. The government has certain rights in the invention.

INTRODUCTION

Real-time monitoring of pollutant, toxic and flammable gases is important for health and safety of industrial workers and of the general population. Small, lightweight, fast, low-power, low-cost sensors would enable ubiquitous monitoring of these gases, which would allow for prevention of exposure or explosions and aid in rapid response to hazardous leaks. Currently, there are many methods of detecting such gases, but most sensors suffer either from slow response times, high power consumption, high cost and/or inability to operate in harsh conditions.

Hydrogen sulfide ($H_2S$) is a naturally occurring gas found in oil deposits and natural gas fields. It is extremely toxic at concentrations as low as hundreds of parts per million. However, its concentration in natural gas can be up to 90%. Workers may be exposed to $H_2S$ in many industrial processes (oil and natural gas drilling and refining, sewage treatment, paper milling, and many others), and it is potentially lethal in concentrations as low as 320 ppm. $H_2S$ is also flammable, corrosive, and low-lying so that high concentrations may develop over time. Although $H_2S$ can be detected by the human nose at levels as low as 0.5 ppb, for concentrations above 100-150 ppm, the concentration around which $H_2S$ begins to have damaging health effects, $H_2S$ paralyzes the olfactory nerve after a few inhalations, disabling the sense of smell. Personal monitoring of $H_2S$ in industrial situations would facilitate worker safety.

SUMMARY

Gas sensors are provided. The gas sensors include a gas sensing element having metal oxide nanoparticles and a thin-film heating element. Systems that include the gas sensors, as well as methods of using the gas sensors, are also provided. Embodiments of the present disclosure find use in a variety of different applications, including detecting whether an analyte is present in a gaseous sample.

The gas sensor (right) included a suspended polysilicon thin-film heating element coated with silicon nitride and had a 2 μm sensing gap between the metal sensor contacts.

Figure 15:
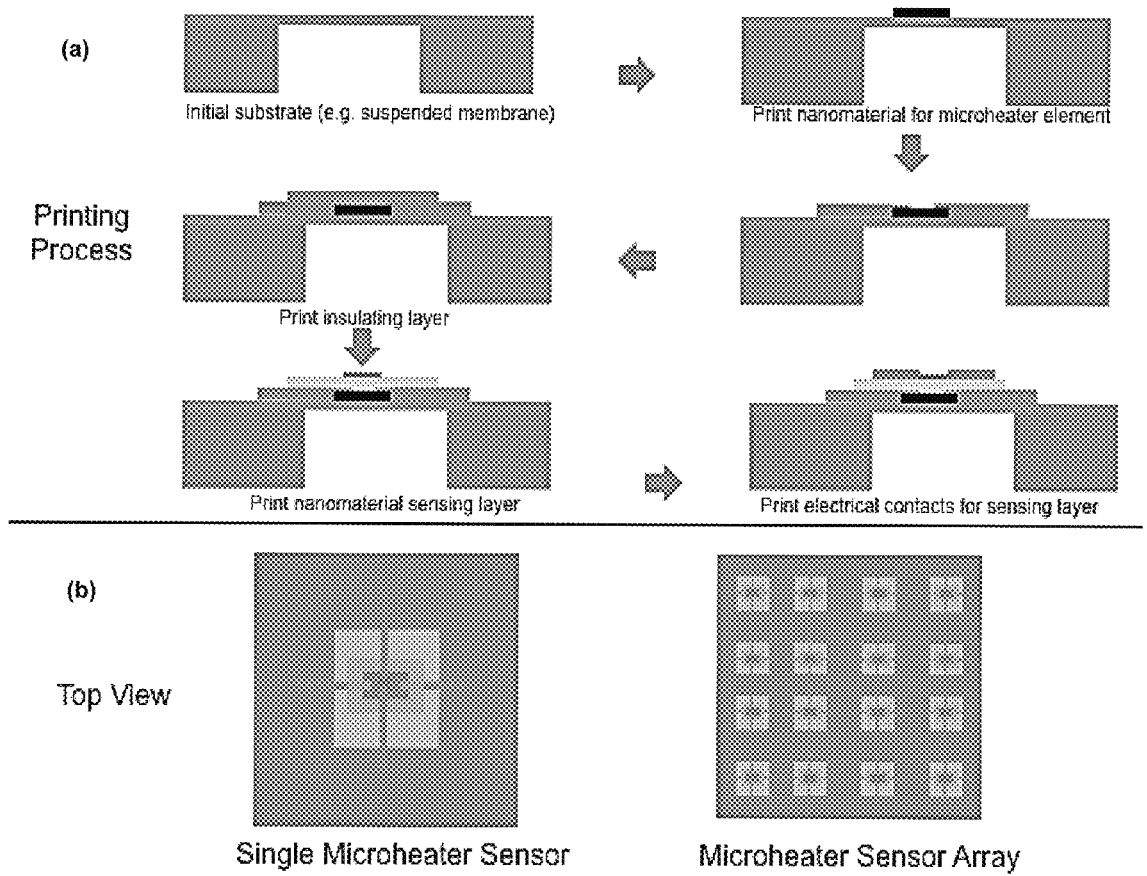

FIG. 15(a) shows a process flow diagram for producing a gas sensor using a printing fabrication process, according to embodiments of the present disclosure. FIG. 15(b) shows a top view of a single sensor (left) and a sensor array that includes 16 gas sensors (right).

Figure 16:
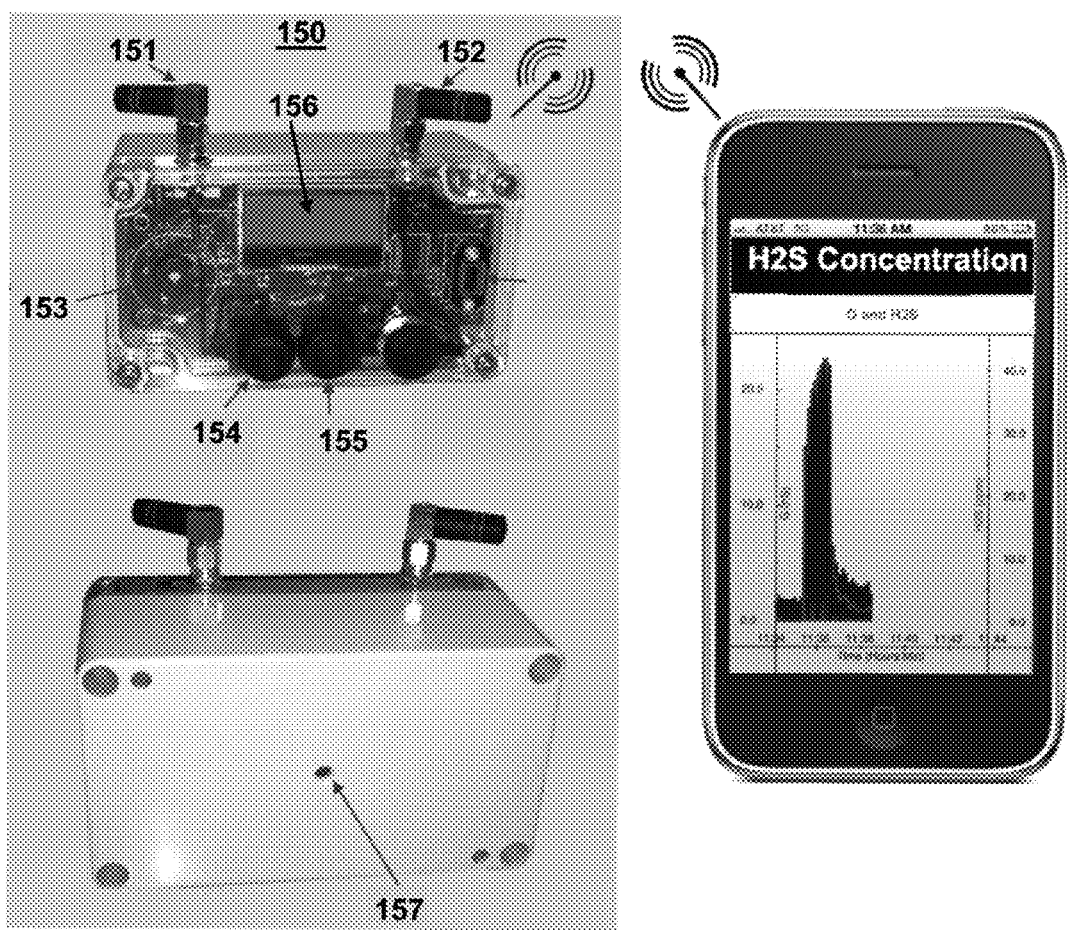

FIG. 16 shows an image of a gas sensing system configured to communicate wirelessly with a smart phone, according to embodiments of the present disclosure. Hydrogen sulfide concentration data taken with the gas sensor system are transmitted over a WiFi radio and plotted in real-time using a custom app on the smart phone.

DETAILED DESCRIPTION

Gas sensors are provided. The gas sensors include a gas sensing element having metal oxide nanoparticles and a thin-film heating element. Systems that include the gas sensors, as well as methods of using the gas sensors, are also provided. Embodiments of the present disclosure find use in a variety of different applications, including detecting whether an analyte is present in a gaseous sample.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Gas Sensors

Gas sensors of the present disclosure include a gas sensing element that includes metal oxide nanoparticles, and a thin-film heating element. In certain embodiments, the gas sensor is configured to detect an analyte in a sample, such as a particular gas of interest in a sample, such as a multi-component gaseous stream made up of a two or more different gasses. For example, the gas sensor may be configured to detect hydrogen sulfide ($H_2S$). Other gases (i.e., gaseous analytes) of interest that may be detected by the gas sensor include, but are not limited to, hydrogen ($H_2$), propane ($C_3H_8$), nitrogen dioxide ($NO_2$), ammonia ($NH_3$), trimethylamine $(CH_3)_3N$, 2-methylpyrazine

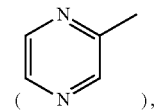

, nitric oxide (NO), methanethiol ($CH_3SH$), ethanol ($C_2H_5OH$), 1,1,1,2-tetrafluoroethane (Refridgerant-134a; $CH_2FCF_3$), ozone ($O_3$), carbon monoxide (CO), dimethyl disulfide ($CH_3SSCH_3$), acetone ($CH_3COCH_3$), hexanal ($C_5H_{11}CHO$), propene ($C_3H_6$), sulfur dioxide ($SO_2$), carbon dioxide ($CO_2$), and the like. The gas sensor may be configured to detect one or more of the above gases individually or substantially simultaneously, as described in more detail below.

Embodiments of the gas sensor include a gas sensing element. In certain embodiments, the gas sensing element includes metal oxide nanoparticles. By "nanoparticle" is meant that the metal oxide particles have dimensions ranging from 1 nm to 1000 nm. For example, the nanoparticles may have an average diameter of 1000 nm or less, such as 900 nm or less, or 800 nm or less, or 700 nm or less, or 600 nm or less, or 500 nm or less, or 400 nm or less, or 300 nm or less, or 200 nm or less, or 100 nm or less, or 50 nm or less. In certain instances, the metal oxide nanoparticles have an average diameter of 100 nm or less. In some instances, the average diameter is 1 nm or greater, such as 5 or 10 nm or greater. By "average" is meant the arithmetic mean.

In certain embodiments, the nanoparticles are arranged on the surface of a substrate (e.g., on a surface of the thin-film heating element or insulation layer, as described in more detail below). The nanoparticles may be arranged in a layer of nanoparticles, such as one or more layers of nanoparticles on the surface of the substrate. For example, the layer of nanoparticles may be a closely packed layer of nanoparticles on the surface of the substrate, such that the layer is substantially continuous (e.g., there are substantially no gaps between adjacent nanoparticles). For instance, nanoparticles in a layer may be in contact with surrounding adjacent nanoparticles. In certain embodiments, the nanoparticles are arranged in a discontinuous layer on the surface of the substrate. For example, nanoparticles in a discontinuous layer may be dispersed such that one or more lateral sides of the nanoparticles do not substantially contact surrounding nanoparticles. In some instances, a discontinuous layer may include one or more groupings (e.g., islands) of nanoparticles surrounded by one or more regions of the substrate surface. In certain cases, the groupings of nanoparticles may be dispersed such that the groupings of nanoparticles do not substantially contact surrounding groupings of nanoparticles. In other cases, the groupings of nanoparticles may be interconnected by one or more bridges of nanoparticles to form a substantially contiguous layer on the surface of the substrate.

In certain embodiments, the layer of nanoparticles on the substrate surface has a density of $1\times10^{10}$ nanoparticles/cm$^2$ or less, such as $7\times10^9$ nanoparticles/cm$^2$ or less, or $5\times10^9$ nanoparticles/cm$^2$ or less, or $3\times10^9$ nanoparticles/cm$^2$ or less, including $1\times10^9$ nanoparticles/cm$^2$ or less, or $7\times10^8$ nanoparticles/cm$^2$ or less, or $5\times10^8$ nanoparticles/cm$^2$ or less, or $3\times10^8$ nanoparticles/cm$^2$ or less, or $1\times10^8$ nanoparticles/cm$^2$ or less, or $7\times10^7$ nanoparticles/cm$^2$ or less, or $5\times10^7$ nanoparticles/cm$^2$ or less, or $3\times10^7$ nanoparticles/cm$^2$ or less, or $1\times10^7$ nanoparticles/cm$^2$ or less, or $7\times10^6$ nanoparticles/cm$^2$ or less, or $5\times10^6$ nanoparticles/cm$^2$ or less, or $3\times10^6$ nanoparticles/cm$^2$ or less, or $1\times10^6$ nanoparticles/cm$^2$ or less, or $7\times10^5$ nanoparticles/cm$^2$ or less, or $5\times10^5$ nanoparticles/cm$^2$ or less, or $3\times10^5$ nanoparticles/cm$^2$ or less, or $1\times10^5$ nanoparticles/cm$^2$ or less.

In certain embodiments, the nanoparticles have a shape that is substantially symmetrical. For example, the nanoparticles may be substantially spherical. By substantially spherical is meant that the nanoparticles have a three-dimensional shape that approximates a sphere. In some instances, the nanoparticles have an average diameter ranging from 1 nm to 500 nm, or 1 nm to 250 nm, 1 nm to 100 nm, or 1 nm to 75 nm, such as from 1 nm to 50 nm, including from 1 nm to 25 nm, or from 1 nm to 10 nm. In certain embodiments, the spherical nanoparticles have an average diameter of 100 nm. By "average diameter" is meant the arithmetic mean diameter. In some cases, the nanoparticles have a surface area to volume ratio of 0.5 or less, such as 0.4 or less, including 0.3 or less, or 0.2 or less, or 0.1 or less, or 0.09 or less, or 0.08 or less, or 0.07 or less, or 0.06 or less, or 0.05 or less. In some instances, the nanoparticles have a surface area to volume ratio of 0.06 or less.

In certain embodiments, the nanoparticles have a shape that is an elongated shape. By elongated shape is meant a particle that has a length that is longer than its width. For instance, an elongated nanoparticle may have an aspect ratio, which is the ratio of the length of the nanoparticle to the width of the nanoparticle. In certain embodiments, the elongated nanoparticle has an aspect ratio greater than 1, such as 1.5 or more, including 2 or more, or 2.5 or more, or 3 or more, or 3.5 or more, or 4 or more, or 4.5 or more, or 5 or more, or 6 or more, or 7 or more, or 8 or more, or 9 or more, or 10 or more. For example, the elongated nanoparticle may have an aspect ratio of 2 or more. In certain embodiments, the elongated nanoparticle has an aspect ratio ranging from 1 to 10, such as from 1 to 7, including from 1 to 5, or from 1 to 3.

In some cases, the elongated nanoparticle has an elongated shape, such as, but not limited to, a cylinder (e.g., a nanocylinder) or a rod (e.g., a nanorod). In some embodiments, the elongated nanoparticle has a cross-sectional profile (e.g., a cross section that intersects the longitudinal axis of the elongated nanoparticle) that has a shape that is substantially circular. Other cross-sectional profiles are possible, such as, but not limited to, an elongated nanoparticle that has a cross-sectional profile in the shape of an ellipse, a rectangle, a square, an irregular shape, and the like.

In some embodiments, the elongated nanoparticle has a length ranging from 1 nm to 1000 nm, including from 1 nm to 750 nm, or from 1 nm to 500 nm, or from 1 nm to 250 nm, or from 1 nm to 100 nm, such as from 10 nm to 100 nm, or from 10 nm to 75 nm. For instance, the elongated nanoparticle may have a length ranging from 1 nm to 250 nm, such as a length of 100 nm. In some embodiments, the elongated nanoparticle has a width ranging from 1 nm to 1000 nm, including from 1 nm to 750 nm, or from 1 nm to 500 nm, or from 1 nm to 250 nm, or from 1 nm to 100 nm, such as from 10 nm to 75 nm, or from 10 nm to 50 nm. For instance, the elongated nanoparticle may have a width ranging from 1 nm to 100 nm, such as a width of 50 nm.

In certain embodiments, the nanoparticles are metal oxide nanoparticles (i.e., the nanoparticles are composed of a metal oxide material). In some instances, the metal oxide is tungsten oxide (also known as tungsten trioxide; $WO_3$). In these instances, the gas sensor may be configured to detect hydrogen sulfide. The gas sensing element may include tungsten oxide and/or other types of metal oxide nanoparticles, such as, but not limited to, tin dioxide ($SnO_2$), titanium dioxide ($TiO_2$), indium(III) oxide ($In_2O_3$), palladium-tin dioxide-antimony ($Pd$—$SnO_2$—$Sb$), iron(III) oxide ($Fe_2O_3$), zinc oxide ($ZnO$), bismuth(III) oxide-molybdenum trioxide ($Bi_2O_3$—$MoO_3$), combinations thereof, and the like.

In certain embodiments, the gas sensing element includes an additional material. The additional material may facilitate detection of the analyte of interest by the metal oxide nanoparticles. For example, the additional material may be a compound that reduces the oxidation temperature of the analyte of interest. In some cases, the additional material may include, but is not limited to, a metal, a metal oxide, a non-metal, an alkali metal carbonate, a lanthanide, a transition metal, a post-transition metal, combinations thereof, and the like. For instance, the additional material may include, but is not limited to, silver (Ag), palladium (Pd), gold (Au), platinum (Pt), ruthenium (Ru), rhodium (Rh), zinc oxide (ZnO), copper(II) oxide (CuO), lanthanum oxide ($La_2O_3$), sulfur (S), cerium(IV) oxide ($CeO_2$), iron(III) oxide ($Fe_2O_3$), silicon dioxide ($SiO_2$), platinum-aluminum oxide ($Pt$—$Al_2O_3$), rubidium carbonate ($Rb_2CO_3$), gold-cobalt oxide ($Au$—$Co_3O_4$), praseodymium oxide ($Pr_6O_{11}$), molybdenum trioxide ($MoO_3$), erbium(III) oxide ($Er_2O_3$), gadolinium(III) oxide ($Gd_2O_3$), bismuth (Bi), molybdenum (Mo), nickel (Ni), tin dioxide ($SnO_2$), cobalt (Co), lanthanum (La), combinations thereof, and the like.

The additional material may be present in the gas sensing element in an amount ranging from 10 weight percent (wt %) or less, such as 9 wt % or less, or 8 wt % or less, or 7 wt % or less, or 6 wt % or less, or 5 wt % or less, or 4 wt % or less, or 3 wt % or less, or 2 wt % or less, or 1 wt % or less, or 0.9 wt % or less, or 0.8 wt % or less, or 0.7 wt % or less, or 0.6 wt % or less, or 0.5 wt % or less, or 0.4 wt % or less, or 0.3 wt % or less, or 0.2 wt % or less, or 0.1 wt % or less. For example, in some cases, the additional material is present in the gas sensing element in an amount of 5 wt % or less. In certain embodiments, the additional material may be present in the gas sensing element in an amount ranging from 5 atomic percent (at %) or less, such as 4 at % or less, or 3 at % or less, or 2 at % or less, or 1 at % or less, or 0.5 at % or less. For example, in some cases, the additional material is present in the gas sensing element in an amount of 3 at % or less.

In some instances, the type of material of the metal oxide nanoparticles may depend on the particular analyte to be detected by the gas sensor. For example, as described above, the gas sensing element may include tungsten oxide ($WO_3$) nanoparticles and the gas sensor may be configured to detect hydrogen sulfide ($H_2S$). Other combinations of metal oxide nanoparticles and additional materials may be included in the gas sensing element for the detection of other target gases, for example as shown in Table 1 below.

TABLE 1

Gas Sensing Element Materials for Detection of Various Target Gases

| Metal Oxide | Additional Material | Target Gas |
|---|---|---|
| $WO_3$ | — | $H_2S$ |
| $SnO_2$ | Ag (3 wt %) Pd (0.3-1 wt %) | $H_2$ and $C_3H_8$ |
| $WO_3$ | — | $NO_2$ |
| $WO_3$ | Au (0.8 wt %) Pt (0.4 wt %) | $NH_3$ |
| $TiO_2$ | Ru (0.5 wt %) | $(CH_3)_3N$ |
| $WO_3$ | Rh (0.4 wt %) | 2-methylpyrazine |
| $WO_3$ | Ru (0.004 wt %) | NO |
| $SnO_2$ | ZnO (3 at %) | $H_2S$ and $CH_3SH$ |
| $SnO_2$ | CuO (5 wt %) | $H_2S$ |
| $SnO_2$ | $La_2O_3$ (5 wt %) | $C_2H_5OH$ |
| $SnO_2$ | S (1 at %) and Pd (1 wt %) | $CH_2FCF_3$ |
| $In_2O_3$ | $CeO_2$ (3 at %) and $Fe_2O_3$ (3 at %) | $O_3$ |
| $Pd$—$SnO_2$—$Sb$ | $SiO_2$ (coating) | $H_2$ |
| $SnO_2$ | 0.5Pt—$Al_2O_3$ (coating) | $C_3H_8$ |
| $In_2O_3$ | $Rb_2CO_3$ (5 wt %) | CO |
| $In_2O_3$ | Au (0.04 wt %)—$Co_3O_4$ (0.5 wt %) | CO |
| $Fe_2O_3$ | $Pr_6O_{11}$ (5 wt %) | $CH_3SSCH_3$ |
| ZnO | $MoO_3$ (5 wt %) and $WO_3$ (5 wt %) | $CH_3COCH_3$ |
| ZnO | $Er_2O_3$ (5 wt %) and $Gd_2O_3$ (5 wt %) | $C_5H_{11}CHO$ |
| $Bi_2O_3$—$MoO_3$ | Bi/Mo (1 wt %) | $C_3H_6$ |
| $TiO_2$ | — | CO |
| $WO_3$ | Pt, Pd, Au | CO |
| $SnO_2$ | Pt | CO |
| $WO_3$ | Pt | $SO_2$ |
| $SnO_2$ | Ni | $SO_2$ |
| ZnO | — | $SO_2$ |
| $TiO_2$ | Pd | $NO_2$ |
| $WO_3$ | Au | $NO_2$ |
| $TiO_2$ | $WO_3$ | $NO_2$ |
| ZnO | $SnO_2$ | $NH_3$ |
| $SnO_2$ | Co, La | $CO_2$ |
| $TiO_2$ | $WO_3$ | $CO_2$ |
| $SnO_2$ | Ag | $H_2S$ |
| $In_2O_3$ | — | $H_2S$ |
| $SnO_2$ and ZnO | Ag, Cu, Mo, Pt | $H_2$, $CH_4$, $C_3H_8$ |

Other combinations of metal oxide nanoparticles and/or additional materials may be included in the gas sensing element for the detection of various target gases as desired.

In certain embodiments, the gas sensing element includes one or more electrodes. The electrodes may be configured to detect a signal indicative of the presence of an analyte of interest in a sample (e.g., a gas of interest in a sample). For example, the electrodes may be configured to detect a change in electrical resistance of the gas sensing element. The resistance of the gas sensing element may be at an initial value before exposure to an analyte or a sample suspected of containing the analyte. After exposing the sensor to the analyte, the analyte may contact (e.g., may be adsorbed on) the gas sensing element (e.g., the metal oxide nanoparticles of the gas sensing element) and may cause a detectable change in the resistance of the gas sensing element. In certain embodiments, the gas sensing element includes a first electrode and a second electrode with the metal oxide nanoparticles disposed between the first electrode and the second electrode. As described above, adsorption of the analyte of interest on the metal oxide nanoparticles may cause a detectable signal, such as a detectable change in the resistance of the gas sensing element.

In certain embodiments, each electrode has an elongated shape. An elongated electrode is one that has a length that is longer than its width. For instance, an elongated electrode may have a length to width ratio greater than 1, such as 5 or more, including 10 or more, or 25 or more, or 50 or more, or 75 or more, or 100 or more, or 125 or more, or 150 or more, or 175 or more, or 200 or more. In some instances, an electrode has a length to width ratio of 25 or more, for example a length to width ratio of 25 or a length to width ratio of 100. In certain embodiments, an electrode has a length of 50 μm or more, such as 75 μm or more, including 100 μm or more, or 150 μm or more, or 200 μm or more, or 250 μm or more, or 500 μm or more, or 750 μm or more, or 1000 μm or more, or 1500 μm or more. For example, an electrode may have a length of 100 μm or more, such as a length of 100 μm or a length of 1000 μm. In certain embodiments, an electrode has a width of 25 μm or less, such as 20 μm or less, including 15 μm or less, or 10 μm or less, or 5 μm or less, or 4 μm or less, or 3 μm or less, or 2 μm or less, or 1 μm or less. For example, an electrode may have a width of 10 μm or less, such as a width of 10 μm or a width of 5 μm.

In certain cases, an electrode is substantially linear. As such, the electrode may be substantially linear (see e.g., FIG. 4 and FIG. 9) with dimensions (e.g., length, width and thickness) as described above. For example, a substantially linear electrode may have a thickness of 250 nm or less, such as a thickness of 250 nm or a thickness of 200 nm, a length of 100 μm or more, such as a length of 100 μm, and a width of 10 μm or less, such as a width of 10 μm or a width of 5 μm.

As indicated above, in certain embodiments, the gas sensing element includes a first electrode and a second electrode with the metal oxide nanoparticles disposed between the first electrode and the second electrode. For instance, the first and second electrodes may be disposed such that they are a distance apart from each other. In some instances, the first and second electrodes are disposed such that one end of the first electrode is spaced a distance apart from an opposing end of the second electrode. In some cases, as described above, the first and second electrodes are elongated electrodes. In these embodiments, each of the first and second electrodes may have a first end that is operatively connected to the gas sensor system and a second sensing end configured to detect the presence of an analyte of interest (e.g., configured to detect a change in signal when the analyte of interest contacts the metal oxide nanoparticles as described above). In certain instances, the sensing ends of the electrodes are spaced a distance apart from each other, as described above. In some cases, the distance between the sensing ends of the electrodes is 10 μm or less, such as 7 μm or less, including 5 μm or less, or 4 μm or less, or 3 μm or less, or 2 μm or less, or 1 μm or less. In certain instances, the distance between the sensing ends of the electrodes is 4 μm or less. In other embodiments, the distance between the sensing ends of the electrodes is 2 μm or less.

In certain embodiments, an electrode of the gas sensor is made of an electrically conductive material. In some instances, the electrode is composed of a metal, such as, but not limited to, platinum, gold, silver, copper, and the like. In certain cases, the electrode is composed of platinum. In certain cases, the electrode is disposed on the thin-film heating element. In some instances, the electrode is disposed on an insulation layer between the thin-film heating element and the electrodes of the gas sensing element. As described in more detail below, the insulation layer may be disposed between the gas sensing element (e.g., the electrodes) and the thin-film heating element.

In certain embodiments, the gas sensor includes a thin-film heating element. By "thin-film" is meant a layer of material that has a thickness of 10 μm or less, such as 5 μm or less, including 1 μm or less, or 750 nm or less, or 500 nm or less, or 250 nm or less, or 200 nm or less, or 150 nm or less, or 100 nm or less, or 50 nm or less, or 25 nm or less, or 10 nm or less. In some instances, the thin-film heating element has a thickness of 250 nm or less, for example a thickness of 250 nm or a thickness of 200 nm.

In certain embodiments, the thin-film heating element has an elongated shape. An elongated thin-film heating element is one that has a length that is longer than its width. For instance, an elongated thin-film heating element may have a length to width ratio greater than 1, such as 5 or more, including 10 or more, or 25 or more, or 50 or more, or 75 or more, or 100 or more, or 125 or more, or 150 or more, or 175 or more, or 200 or more. In some instances, the thin-film heating element has a length to width ratio of 25 or more, for example a length to width ratio of 25 or a length to width ratio of 100. In certain embodiments, the thin-film heating element has a length of 50 μm or more, such as 75 μm or more, including 100 μm or more, or 150 μm or more, or 200 μm or more, or 250 μm or more, or 500 μm or more, or 750 μm or more, or 1000 μm or more, or 1500 μm or more. For example, the thin-film heating element may have a length of 100 μm or more, such as a length of 100 μm or a length of 1000 μm. In certain embodiments, the thin-film heating element has a width of 25 μm or less, such as 20 μm or less, including 15 μm or less, or 10 μm or less, or 5 μm or less, or 4 μm or less, or 3 μm or less, or 2 μm or less, or 1 μm or less. For example, the thin-film heating element may have a width of 10 μm or less, such as a width of 10 μm or a width of 5 μm.

Figure 1:
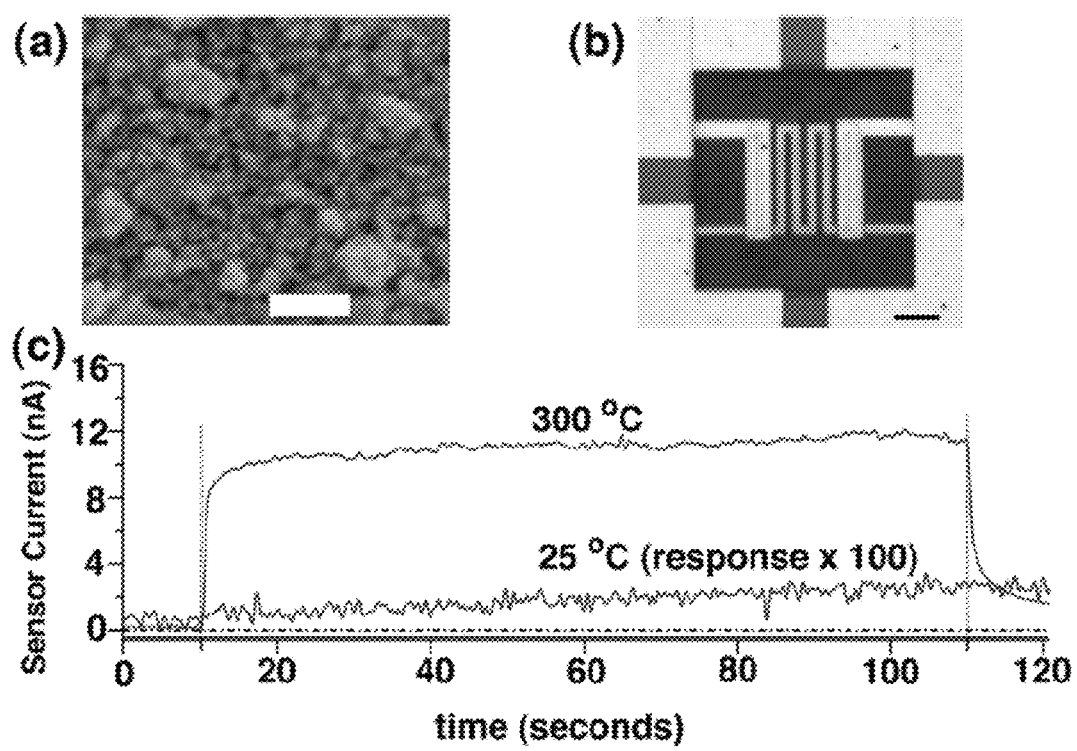
FIG. 1(a) shows a SEM image of $WO_3$ nanoparticles deposited on a substrate, according to embodiments of the present disclosure. Scale bar is 500 nm.
FIG. 1(b) shows an optical image of a microhotplate. The Pt heating element was suspended on a 500-nm-thick silicon nitride membrane. A 500-nm thick $SiO_2$ insulating layer separated the gold lead electrodes from the Pt heating element. Scale bar is 100 μm.
FIG. 1(c) shows a graph of the sensor current at room temperature and 300° C. to a 100-second-long exposure of 50 ppm $H_2S$. The response at room temperature was small and slow with a low signal-to-noise ratio and long recovery time. The response at 300° C. was large and fast, with a $\Delta I/I_0$ of 80 and a $T_{50}$ of 700 ms, with a high signal-to-noise and short recovery time.

In certain cases, the thin-film heating element is substantially linear. As such, the thin-film heating element may be substantially linear (see e.g., FIG. 4 and FIG. 9) with dimensions (e.g., length, width and thickness) as described above. For example, a substantially linear thin-film heating element may have a thickness of 250 nm or less, such as a thickness of 250 nm or a thickness of 200 nm, a length of 100 μm or more, such as a length of 100 μm, and a width of 10 μm or less, such as a width of 10 μm or a width of 5 μm. In other embodiments, the thin-film heating element may have a non-linear shape, such as, but not limited to a serpentine shape (see e.g., FIG. 1(b)), a curved shape, and the like. A non-linear thin-film heating element may also have dimensions as described above, where the total length may be measured as the sum of the lengths of the non-linear portions of the thin-film heating element. For instance, a non-linear thin-film heating element may have a thickness of 250 nm or less, such as a thickness of 250 nm or a thickness of 200 nm, a length of 100 μm or more, such as a length of 1000 μm, and a width of 10 μm or less, such as a width of 10 μm or a width of 5 μm. In some cases, due to a non-linear shape of the thin-film heating element, a thin-film heating element having a relatively long total length may be fit into an area with dimensions less than the total length of the thin-film heating element. For instance, FIG. 1(b) shows a thin-film heating element with a serpentine shape that has a total length of 1000 μm or more, which occupies a 250 μm×250 μm area.

The thin-film heating element may be made of a material that converts electricity into heat. For example, electric current passed through the heating element encounters resistance, which results in heating of the element. In some instances, the thin-film heating element is composed of a metal, a metalloid or a non-metal, such as, but not limited to polysilicon, platinum, carbon (e.g., carbon nanotubes), graphene, and the like. In some embodiments, the thin-film heating element is composed of polysilicon. In other embodiments, the thin-film heating element is composed of platinum.

In certain embodiments, the thin-film heating element is configured as a beam (or bridge) suspended over a void in a substrate. The void may be a hole in the substrate, or the void may be a depression or trench in the substrate that extends below the surface of the substrate. The thin-film heating element may have a first end that contacts the substrate on one side of the void and a second end that contacts the substrate at an opposing side of the void, such that at least a portion of the thin-film heating element between the first and second ends is not in contact with the surface of the substrate. In certain instances, substantially the entire length of the thin-film heating element is suspended over the void (i.e., not in contact with the surface of the substrate), with only the ends of the thin-film heating element contacting the substrate. The thin-film heating element may be coated with an insulation material as described in more detail below.

In other embodiments, the thin-film heating element is disposed on a membrane. In some instances, the membrane is suspended over the surface of the substrate, such that at least the portion of the membrane which contacts the thin-film heating element on one side of the membrane does not contact the surface of the substrate on the opposing side of the membrane. In certain cases, the membrane may be composed of an insulation material, such as, but not limited to silicon nitride, silicon dioxide, and the like. In certain embodiments, the membrane is composed of silicon nitride. In some instances, a thin-film heating element that is disposed on a membrane may have an additional insulation layer disposed on top of the thin-film heating element. As such, the thin-film heating element may be sandwiched between the membrane and an insulation layer. The insulation layer may be composed of an insulation material, such as, but not limited to silicon dioxide, silicon nitride, and the like. In some cases, the insulation layer is composed of silicon dioxide.

In certain embodiments, the thin-film heating element is configured to heat to a temperature significantly greater that ambient temperature. For example, the thin-film heating element may be configured to heat to a temperature compatible with the gas sensing assay to be performed. In some instances, the thin-film heating element is configured to heat to a temperature of 100° C. or more, such as 150° C. or more, including 200° C. or more, or 250° C. or more, or 300° C. or more, or 350° C. or more, or 400° C. or more, or 450° C. or more, or 500° C. or more. In certain cases, the thin-film heating element is configured to heat to a temperature of 300° C. or more.

In certain embodiments, the thin-film heating element is configured to have a low peak power consumption. For instances, the thin-film heating element may be configured to have a peak power consumption such that the gas sensor may be operated using a portable power supply, such as a battery. In certain cases, the thin-film heating element is configured to have a peak power consumption of 100 mW or less, such as 90 mW or less, including 80 mW or less, or 70 mW or less, or 60 mW or less, or 50 mW or less, or 40 mW or less or 30 mW or less, or 20 mW or less, or 10 mW or less, or 5 mW or less, or 4 mW or less, or 3 mW or less, or 2 mW or less, or 1 mW or less. In some instances, the thin-film heating element is configured to have a peak power consumption of 40 mW or less. In other instances, the thin-film heating element is configured to have a peak power consumption of 2 mW or less.

In certain embodiments, the thin-film heating element is configured to have a low average power consumption. For instances, the thin-film heating element may be configured to have an average power consumption such that the gas sensor may be operated using a portable power supply, such as a battery. In certain cases, the thin-film heating element is configured to have an average power consumption of 50 mW or less, such as 40 mW or less, including 30 mW or less, or 20 mW or less, or 10 mW or less, or 5 mW or less, or 4 mW or less, or 3 mW or less, or 2 mW or less, or 1 mW or less, or 750 µW or less, or 500 µW or less, or 250 µW or less, or 100 µW or less. In some instances, the thin-film heating element is configured to have an average power consumption of 10 mW or less. In other instances, the thin-film heating element is configured to have an average power consumption of 250 µW or less.

In certain embodiments, the thin-film heating element is a pulsed thin-film heating element. By "pulsed" is meant that the thin-film heating element is configured to be repeatedly activated and deactivated over a period of time. The pulsed thin-film heating element may have a duty cycle, which is the percent of time that the thin-film heating element is in an active state as a fraction of the total time. In some instances, the thin-film heating element has a duty cycle of 25% or less, such as 20% or less, including 15% or less, or 10% or less, or 5% or less, or 3% or less, or 1% or less, or 0.5% or less, or 0.3% or less, or 0.1% or less. In certain cases, the thin-film heating element has a duty cycle of 20% or less, such as about 15%. In other cases, the thin-film heating element has a duty cycle of 0.1% or less.

The pulsed thin-film heating element may also have a frequency, which is the number of times per second that the thin-film heating element is activated. In some instances, the thin-film heating element has a frequency of 0.1 Hz or more, such as 0.2 Hz or more, including 0.3 Hz or more, or 0.4 Hz or more, or 0.5 Hz or more, or 0.6 Hz or more, or 0.7 Hz or more, or 0.8 Hz or more, or 0.9 Hz or more, or 1 Hz or more, or 2 Hz or more, or 3 Hz or more, or 4 Hz or more, or 5 Hz or more, or 6 Hz or more, or 7 Hz or more, or 8 Hz or more, or 9 Hz or more, or 10 Hz or more, or 25 Hz or more, or 50 Hz or more, or 75 Hz or more, or 100 Hz or more. In certain cases, the thin-film heating element has a frequency of 0.1 Hz or more. In other cases, the thin-film heating element has a frequency of 1 Hz or more.

In certain embodiments, the gas sensor includes an insulation layer. The insulation layer may be between the gas sensing element and the thin-film heating element. The insulation layer may be configured to electrically isolate the thin-film heating element from the gas sensing element. In some instances, the insulation layer surrounds the thin-film heating element. The insulation layer may be composed of an insulation material, such as, but not limited to silicon dioxide, silicon nitride, polyimide, and the like. In certain instances, the insulation layer is composed of silicon nitride.

In certain embodiments, the gas sensor is configured to be thermally efficient. For example, the thin-film heating element may be configured to by thermally efficient. By "thermal efficiency" is meant the temperature increase of the device per amount of power input into the device. In some cases, the gas sensor (e.g., the thin-film heating element of the gas sensor) has a thermal efficiency ranging from 10° C./mW to 1000° C./mW, such as 10° C./mW to 900° C./mW, including 10° C./mW to 800° C./mW, or 10° C./mW to 700° C./mW, or 10° C./mW to 600° C./mW, or 10° C./mW to 500° C./mW, or 20° C./mW to 500° C./mW, or 30° C./mW to 500° C./mW, or 30° C./mW to 400° C./mW, or 30° C./mW to 300° C./mW, or 30° C./mW to 200° C./mW, or 30° C./mW to 100° C./mW. In certain instances, the gas sensor (e.g., the thin-film heating element of the gas sensor) has a thermal efficiency ranging from 30° C./mW to 200° C./mW.

In certain embodiments, the gas sensor (e.g., the thin-film heating element of the gas sensor) is configured to have a short thermal response time. For example, the gas sensor (e.g., the thin-film heating element of the gas sensor) may be configured to have a thermal response time of 100 seconds (s) or less. By "thermal response time" is meant the time required for a device (e.g., thin-film heating element) to reach a given temperature after the device is activated. In some cases, the gas sensor (e.g., the thin-film heating element of the gas sensor) is configured to have a thermal response time of 100 s or less, such as 90 s or less, including 80 s or less, or 70 s or less, or 60 s or less, or 50 s or less, or 40 s or less, or 30 s or less, or 20 s or less, or 10 s or less, or 7 s or less, or 5 s or less, or 4 s or less, or 3 s or less, or 2 s or less, or 1 s or less, or 750 ms or less, or 500 ms or less, or 250 ms or less, or 100 ms or less, or 50 ms or less, or 10 ms or less, or 1 ms or less, or 750 µs or less, or 500 µs or less, or 250 µs or less, or 100 µs or less, or 50 µs or less, or 25 µs or less, or 10 µs or less, or 1 µs or less. In certain instances, the gas sensor (e.g., the thin-film heating element of the gas sensor) is configured to have a thermal response time of 2 s or less. In other embodiments, the gas sensor (e.g., the thin-film heating element of the gas sensor) is configured to have a thermal response time of 50 µs or less.

In certain embodiments, the gas sensor is configured to detect very low levels of a target gas. For instance, the gas sensor may be configured to have a limit of detection of 500 parts per million (ppm) or less. By "limit of detection" is meant the lowest quantity of a substance that can be distinguished from the absence of that substance (e.g., a blank value). In certain instances, the gas sensor is configured to have a limit of detection of 500 ppm or less, such as 400 ppm or less, including 300 ppm or less, or 200 ppm or less, or 100 ppm or less, of 75 ppm or less, or 50 ppm or less, or 25 ppm or less, or 20 ppm or less, or 15 ppm or less, or 10 ppm or less, or 5 ppm or less, or 1 ppm or less, or 500 ppb or less, or 100 ppb or less, or 50 ppb or less, or 10 ppb or less, or 1 ppb or less. In certain cases, the gas sensor is configured to have a limit of detection of 1 ppm or less.

Gas Sensor Systems

Aspects of the present disclosure include a gas sensor system. The gas sensor system includes one or more gas sensors as described herein. For example, the gas sensor system may include one gas sensor. In other embodiments, the gas sensor system includes two or more gas sensors, such as 3 or more, including 4 or more, or 5 or more, or 6 or more, or 7 or more, or 8 or more, 9 or more, or 10 or more, or 15 or more, or 20 or more, or 25 or more, or 30 or more, or 40 or more, or 50 or more gas sensors. In some cases, the gas sensor system includes 8 gas sensors.

In certain embodiments, the subject gas sensor system is a chip (e.g., a sensor chip). By "chip" or "sensor chip" is meant a system that includes a substrate surface which displays one or more distinct gas sensors on the substrate surface. In certain embodiments, the system includes a substrate surface with an array of gas sensors. An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., gas sensors) may be separated by intervening spaces. Any given substrate may carry one, two, four or more arrays disposed on a front surface of the substrate. Depending upon the use, any or all of the arrays may be the same or different from one another and each may contain multiple distinct gas sensors. For example, an array may contain one or more, including two or more, four or more, 8 or more, 10 or more, 15 or more, 20 or more, 25 or more, 30 or more, 40 or more, 50 or more, 70 or more, or 100 or more gas sensors. In certain embodiments, the gas sensors can be arranged into an array with an area of less than 10 cm$^2$, or less than 5 cm$^2$, e.g., less than 1 cm$^2$, including less than 50 mm$^2$, less than 20 mm$^2$, such as less than 10 mm$^2$, or even smaller. For example, array of gas sensors may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 3 mm×3 mm or less, or 1 mm×1 mm or less.

Figure 13:
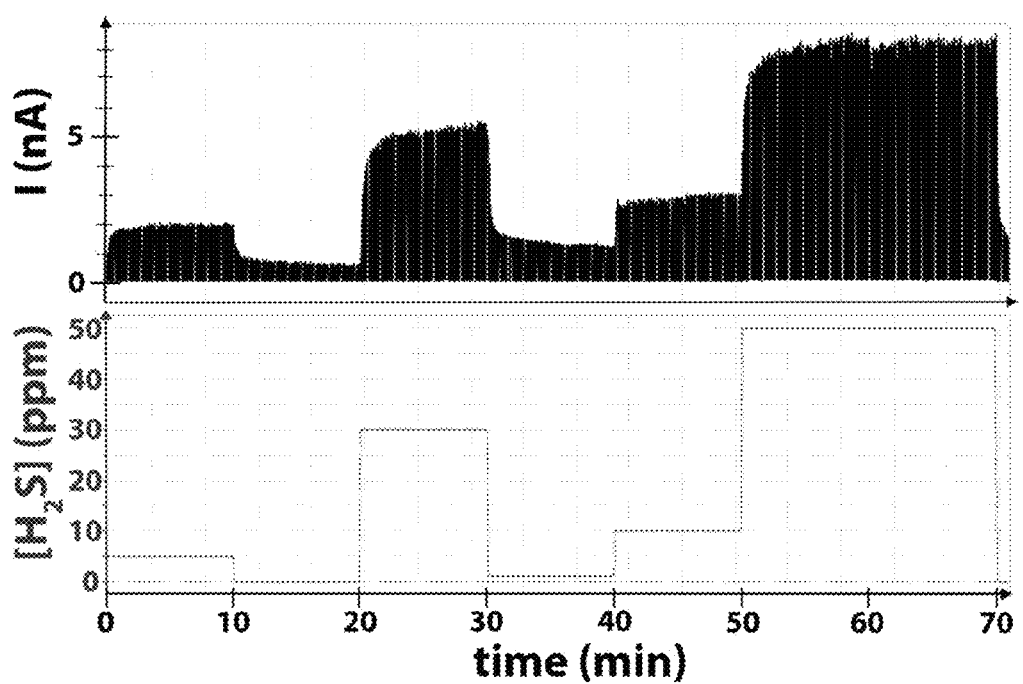
FIG. 13 shows graphs of hydrogen sulfide sensing using a microheated sensor according to embodiments of the present disclosure.
Figure 14:
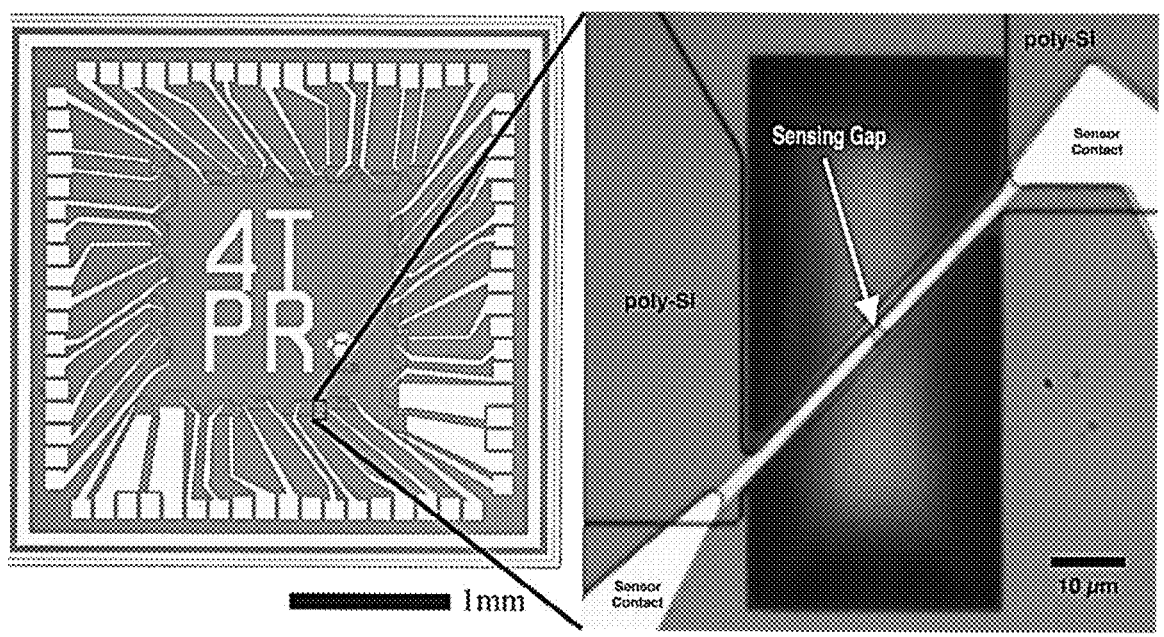
FIG. 14 shows optical images of an array of 12 gas sensors that include polysilicon thin-film heating elements (left), according to embodiments of the present disclosure.

FIG. 14 shows optical images of a silicon-based gas sensor array (left) and an enlarged view of an individual gas sensor (right). The thin-film heating elements included a suspended polysilicon layer, approximately 5 μm wide and 50 μm long. The polysilicon thin-film heating element was isolated from the metal sensor leads by a thin silicon nitride insulation layer. In the center of the thin-film heating element was a 2 μm sensing gap. The sensor was effective for hydrogen sulfide detection when functionalized with tungsten oxide nanoparticles, as shown in FIG. 13. The gas sensor had a peak power of 4 mW and an average power consumption of 4 μW, when heated with a pulsed thin-film heating element.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their oxidation temperature, affinity for the gas sensing element (e.g., metal oxide nanoparticles), and the like. In some instances, the number of analytes is 2 or more, such as 4 or more, 6 or more, 8 or more, 10 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes, or 4 to 10 distinct analytes.

Arrays of gas sensors may be arranged for the multiplex analysis of samples. For example, multiple gas sensors may be arranged in series, such that a sample may be analyzed for the presence of several different analytes in a series of gas sensor devices. In certain embodiments, multiple gas sensors may be arranged in parallel, such that two or more samples may be analyzed at substantially the same time.

In certain embodiments, the gas sensor system includes a controller. The controller may be configured to control the thin-film heating element. For instance, the controller may be configured to control the activation and deactivation of the thin-film heating element. In some cases, the controller is configured to control a pulsed thin-film heating element. For example, the controller may be configured to repeatedly activate and deactivate the thin-film heating element over a period of time. As such, the controller may be configured to activate the thin-film heating element with a duty cycle, as desired. In some instances, the controller is configured to activate the thin-film heating element with a duty cycle of 25% or less, such as 20% or less, including 15% or less, or 10% or less, or 5% or less, or 3% or less, or 1% or less, or 0.5% or less, or 0.3% or less, or 0.1% or less. In certain cases, the controller is configured to activate the thin-film heating element with a duty cycle of 20% or less, such as about 15%. In other cases, the controller is configured to activate the thin-film heating element with a duty cycle of 0.1% or less.

In certain instances, the controller is configured to activate the thin-film heating element with a frequency, as desired. In certain cases, the controller is configured to activate the thin-film heating element with a frequency of 0.1 Hz or more, such as 0.2 Hz or more, including 0.3 Hz or more, or 0.4 Hz or more, or 0.5 Hz or more, or 0.6 Hz or more, or 0.7 Hz or more, or 0.8 Hz or more, or 0.9 Hz or more, or 1 Hz or more, or 2 Hz or more, or 3 Hz or more, or 4 Hz or more, or 5 Hz or more, or 6 Hz or more, or 7 Hz or more, or 8 Hz or more, or 9 Hz or more, or 10 Hz or more, or 25 Hz or more, or 50 Hz or more, or 75 Hz or more, or 100 Hz or more. In some embodiments, the controller is configured to activate the thin-film heating element with a frequency of 0.1 Hz or more. In other cases, the controller is configured to activate the thin-film heating element with a frequency of 1 Hz or more.

In certain embodiments, the gas sensor system is sized to be a portable, hand-held system. An embodiment of a portable gas sensor system is shown in FIG. 16. As shown in FIG. 16, the gas sensor system 150 includes one or more wireless communication devices, such as a WiFi communication device 151, a Zigbee communication device 152, and the like. The gas sensor system 150 also includes a user input 154 configured to allow a user to input commands into the device. The gas sensor system 150 also includes a power button 155 configured to allow a user to turn the gas sensor system 150 on or off. The gas sensor system 150 also includes an audio alarm 153. The audio alarm 153 may be configured to alert a user if the concentration of a detected analyte is equal to or greater than a threshold value. In addition, the gas sensor device 150 includes a display 156. The display 156 may be configured to display a detection result to a user. The detection result may be a qualitative (e.g., yes/no indication) or a quantitative (e.g., concentration) determination of the presence of an analyte in the sample. The gas sensor system 150 may further include a gas sensor port 157. The gas sensor port 157 may be configured to allow a sample of gas to be contacted to a gas sensor inside the gas sensor system 150. In certain embodiments, as shown in FIG. 16, the gas sensor system may be configured to communicate (e.g., wirelessly communicate) with an external device. The external device may be configured to receive data transmitted from the gas sensor system and display the detection results to a user on a display of the external device. In some embodiments, the external device is also configured to control the gas sensor system, such as for example by transmitting commands input into the external device to the gas sensor system, where the gas sensor system may execute such commands. In certain instances, the external device may be a smart phone configured to operate a software application that displays and/or controls the gas sensor system remotely.

Methods

Aspects of embodiments of the present disclosure include a method of detecting whether an analyte is present in a gaseous sample. The method includes contacting a gaseous sample to a gas sensor as described herein to produce a signal. Aspects of the gas sensor and gas sensor system are described above. In some instances, the contacting includes directing a flow of a gaseous sample to contact the gas sensor. Directing the flow of a gaseous sample may include directing the gaseous sample through a flow cell to contact a gas sensor in the flow cell. The gas may be a gaseous sample to be tested for the presence of an analyte of interest, such as a gaseous sample suspected of containing hydrogen sulfide. The flow of the gaseous sample may be directed to contact the surface of the gas sensor where the metal oxide nanoparticles are attached. In certain cases, the directing includes directing the flow of the gaseous sample across (e.g., substantially parallel to) the surface of the gas sensor. In other embodiments, the directing includes directing the flow of the sample to the gas sensor such that the flow of the sample is substantially perpendicular to the surface of the gas sensor.

In certain embodiments, the method includes heating the gas sensing element with the thin-film heating element during the contacting. As such, the gas sensing element may be heated while the gaseous sample is contacted to the gas sensor as described above. In some instances, the method includes activating and deactivating the thin-film heating element. For example, the heating may include repeatedly activating and deactivating the thin-film heating element over a period of time. As such, the method may include activating the thin-film heating element with a certain duty cycle and/or frequency as described above.

Embodiments of the method also include analyzing the signal from the sensor to determine whether the analyte is present in the sample. In some instances, the method includes detecting changes in the signal to determine whether the analyte of interest is present in the sample. For example, the method may include detecting changes in the sensor current over time. In some cases, measuring changes in the sensor current may provide an indication of the presence of the analyte of interest in the sample.

In certain cases, the method further includes quantifying the amount of the analyte of interest in the sample. For example, the quantifying may include determining the amount of the analyte in the sample based on the signal from the sensor. In some instances, the quantifying includes determining the amount of the analyte in the sample based on changes in the signal from the sensor. For instances, the quantifying may include determining the amount of the analyte in the sample based on changes in the sensor current over time. As such, by measuring changes in the sensor current, the concentration of the analyte in the sample may be determined.

In some embodiments, the method includes displaying a result to a user. The result may be a qualitative or quantitative determination of the presence or absence of an analyte in a sample. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which a measurement of the concentration of the analyte is provided to the user.

In certain embodiments, the method includes alerting a user. The method may include alerting a user by activating an alarm if the quantity (e.g., concentration) of the analyte is greater than a threshold value. As described above, the method may include quantifying the analyte in the sample. The method may further include comparing the determined quantity of the analyte to a threshold value. If the quantity of the analyte is below the threshold value, then the alert may not be displayed to the user. If the quantity of the analyte is equal to or greater than a threshold value, then the method may include activating the alarm to alert the user.

In certain embodiments, the method includes applying a bias voltage to the sensor. Measurements of the sensor current to determine the presence and/or quantity of the analyte in the sample may be performed while the bias voltage is applied to the sensor. As such, in some instances, the method includes detecting the current through the sensor as the bias voltage is applied to the sensor. In certain cases, the bias voltage is 10 V or less, such as 7 V or less, or 5 V or less, or 4 V or less, or 3 V or less, or 2.5 V or less, or 2 V or less, or 1.5 V or less, or 1 V or less, or 0.5 V or less, or 0.1 V or less. In some instances, the bias voltage is 2.5 V or less.

In certain embodiments of the method, the contacting includes flowing a gaseous sample through a flow cell comprising the gas sensor. In some instances, the gaseous sample has a flow rate of 1 L/min or more, such as 10 L/min or more, including 25 L/min or more, or 50 L/min or more, or 75 L/min or more, or 100 L/min or more.

Aspects of the present disclosure further include a method for producing a gas sensor as described herein. In certain embodiments, the gas sensor may include layers of elements as described above, such as a gas sensing element, a thin-film heating element, an insulation layer, etc. The layers of the gas sensor may be fabricated using conventional thin film fabrication techniques, such as microelectromechanical (MEMS) fabrication techniques. MEMS fabrication techniques include, but are not limited to, deposition processes (e.g., physical deposition processes or chemical deposition processes), patterning (e.g., lithography, such as photolithography, electron beam lithography, ion beam lithography, X-ray lithography, etc.), etching processes (e.g., isotropic etching, anisotropic etching, hydrofluoric acid etching, electrochemical etching, vapor etching, plasma etching, sputtering, reactive ion etching, etc.), combinations thereof, and the like.

In certain embodiments, the fabrication method includes printing the gas sensor onto the surface of a substrate. For instance, the layers of the gas sensor (e.g., gas sensing element, thin-film heating element, insulation layer, etc.) may be printed onto the surface of a substrate. The layers of the gas sensor may be printed, for instance using inkjet printing processes. An example of the printing of the thin-film heating element, insulation layers, and gas sensing elements is shown schematically in FIG. 15(a). FIG. 15(b) shows a top view of a single sensor (left) and a sensor array that includes 16 gas sensors (right). Starting from a variety of substrates, such as Kapton or silicon wafers with pre-defined thin membranes, the thin-film heating element may be printed first. The thin-film heating element may be printed using high current carrying capacity inks, such as carbon or polysilicon based inks. Then the metal leads may be printed to connect to the thin-film heating element. Once the thin-film heating element is formed, an insulation layer may be printed on top of the thin-film heating element to isolate the thin-film heating element from the gas sensing element. The gas sensing element may then be deposited on the insulation layer. Finally, the metal leads (e.g., electrodes) may be printed to connect to the gas sensing element. The type of gas sensing element can be varied and chosen depending on the type of gas(es) the gas sensor is configured to detect. In some instances, different metal oxide nanoparticles may be deposited on each gas sensor to produce a gas sensor array configured to detect multiple different gases. By printing more than one type of metal oxide nanoparticles onto each gas sensor, the specificity and sensitivity to particular gases of interest can be increased.

In addition to depositing already-synthesized nanomaterials onto the gas sensors as described above, embodiments of the fabrication methods may include producing nanomaterials in situ by depositing reagents and/or catalysts for nanomaterials of interest onto the gas sensors during the fabrication process. For example, gold nanoparticles may be formed by depositing gold salts and sodium citrate, such that the reduction of gold salts with sodium citrate produces gold nanoparticles in situ.

Utility

Gas sensors, gas sensor systems and methods as disclosed herein find use in the detection of an analyte (e.g., gas) of interest in a sample. As described above, the sample may be a gaseous sample to be tested for the presence of an analyte of interest, such as a gaseous sample suspected of containing hydrogen sulfide. As such, gas sensors, systems and methods as disclosed herein find use in the detection of hydrogen sulfide in a gaseous sample. For example, gas sensors, systems and methods as disclosed herein find use in environmental, occupational, and regulatory measurements of analytes of interest (e.g., hydrogen sulfide). Samples may include, but are not limited to, samples obtained from the surrounding environment, samples obtained from gases from industrial processes (e.g., oil and natural gas drilling and refining, sewage treatment, paper milling, etc.), samples obtained from emissions from laboratory processes, and the like. For instance, the gas sensors, systems and methods find use in the monitoring of hydrogen sulfide in samples obtained from the surrounding environment or industrial processes as described above. In some cases, the gas sensors, systems and methods may be used by industrial workers who may be exposed to $H_2S$, the general population who may be near industrial plants or oil refineries, pollution monitoring companies, protections services agencies, and the like.

Gas sensors, gas sensor systems and methods as disclosed herein also find use in the detection of other analytes of interest, such as gases including, but not limited to, hydrogen ($H_2$), propane ($C_3H_8$), nitrogen dioxide ($NO_2$), ammonia ($NH_3$), trimethylamine ($CH_3$)$_3$N, 2-methylpyrazine

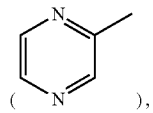

nitric oxide (NO), methanethiol ($CH_3SH$), ethanol ($C_2H_5OH$), 1,1,1,2-tetrafluoroethane (Refridgerant-134a; $CH_2FCF_3$), ozone ($O_3$), carbon monoxide (CO), dimethyl disulfide ($CH_3SSCH_3$), acetone ($CH_3COCH_3$), hexanal ($C_6H_{11}CHO$), propene ($C_3H_6$), sulfur dioxide ($SO_2$), carbon dioxide ($CO_2$), and the like. The gas sensors and gas sensor systems find use in the detection of individual gases as described above. In addition, the gas sensors and gas sensor systems also find use in the detection of two or more gases of interest substantially simultaneously.

Gas sensors, gas sensor systems and methods as disclosed herein find use in alerting a user to the presence of one or more of the gases of interest. As described above, if an analyte of interest is detected by the gas sensor or gas sensor system, an audible and/or visual alert can be displayed to that user. As such, the gas sensors, gas sensor systems and methods as disclosed herein find use in the detection of a potentially hazardous analyte of interest and alerting the user to its presence. As described above, the gas sensors and gas sensor systems may be configured to have a limit of detection of 1 ppm or less. As such, the gas sensors, gas sensor systems and methods as disclosed herein find use in the early detection and warning of a user to the presence of a potentially hazardous analyte of interest in the surrounding environment at a point in time before the level of the analyte in the surrounding environment is a significant health risk to the user, such that the user has sufficient time to take an appropriate course of action to mitigate the potentially hazardous situation.

In certain embodiments, the gas sensors, systems and methods find use in portable gas detection. Low power (e.g., battery operated) gas sensors as described herein may facilitate a reduction in the size and cost of gas sensor systems. In addition, in some instances, the gas sensors, systems and methods disclosed herein require less power and maintenance than conventional systems such as electrochemical cells, photoluminescence, and the like. Portable gas detection may facilitate use of the gas sensors and gas sensor systems disclosed herein by individual users (e.g., industrial workers) who may be exposed to potentially hazardous gases in their working environments.

Kits

Aspects of the present disclosure additionally include kits that have a gas sensor or a gas sensor system as described herein. The kits may further include a power source configured to power the gas sensor or gas sensor system. In certain instances, the power source may be a portable power source, such as a battery. As such, the kits may include a portable gas sensor or a portable gas sensor system as described herein.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

Nanostructures contain large surface areas providing many surface reaction sites. The small length scales increases the effects of surface adsorbates and the low thermal mass enables heating to high temperatures with low power. Nanostructured gas sensors are also more amenable to fabrication on silicon wafers than conventional sensors, and silicon process technology may be used for fabrication. Much of the research into nanomaterials-based sensors has focused on semiconducting metal oxide (SMO) sensors. Tungsten oxide ($WO_3$) is sensitive to $H_2S$ with a low cross-sensitivity to many other gaseous species.

Most SMOs though, including $WO_3$, are insulating at normal temperatures and are semiconducting above about 100-200° C. One method of heating SMOs at low power, which was used here, is to fabricate them on a microheater (e.g., a microhotplate). The microheater generally consisted of a thin membrane, to provide thermal isolation from the substrate, a patterned heating element, and an oxide layer to electrically insulate the heater from the sensing element. Because of the low thermal mass of the nano-structured SMOs, the microheater reaches the target temperature in tens of milliseconds.

The $H_2S$ sensors were made from networks of $WO_3$ nanoparticles fabricated with on-chip microhotplates, which were fast, sensitive, low-power, and manufacturable at low cost. These sensors had a limit of detection below 1 ppm, a measurement range from 0-200 ppm, low cross sensitivity to common gases, response times of only a few seconds, and operated at low power (<10 mW). The hydrogen sulfide sensor included a network of $WO_3$ nanoparticles, shown in FIG. 1(a), deposited between two electrodes on a membrane with an embedded platinum heating element.

To fabricate the $WO_3$ nanoparticle-based $H_2S$ sensor, the $WO_3$ nanoparticles of nominal size 90 nm (MKNano, MKN-WO3-090) were suspended in isopropanol via ultrasonication and were either drop cast or spin cast onto the microhotplate device (Kebaili Corporation, KMHP-100), as shown in FIG. 1(a). The device, shown in FIG. 1(b), included of a film of silicon nitride (500 µm×500 µm×500 nm), a serpentine heating element (250 µm×250 µm) made of platinum that is 10 µm wide and 250 nm tall, followed by a 500-nm-thick layer of $SiO_2$ to isolate the heater from the sensing element. Two gold electrodes, 250 µm wide and 200 µm apart, were the source and drain contacts for the sensing element. The sensing layer was a $WO_3$ nanoparticle network, prepared by depositing $WO_3$ nanoparticles, approximately 90 nm in diameter, onto the microhotplate, using conventional deposition methods.

Hydrogen sulfide gas was delivered to the sensor by a computer-controlled gas delivery system. A cylinder of 500 ppm $H_2S$, balanced in $N_2$, was diluted via mass flow control with air, which had been dried with pressure swing adsorption dryers and passed through an activated carbon scrubber to remove hydrocarbons and other contaminants. The $H_2S$-containing gas stream can also be humidified by a controlled evaporator mixer. Interfering gases can also be introduced into the gas stream. The stream of gas was continuously delivered to the sensor, after which it flowed to a humidity sensor (Vaisala HUMICAP HMT330), and a $H_2S$ reference sensor (Teledyne API101E). Sensor and heater voltage was sourced and current measurements were taken by a Keithley 2602A, which was controlled by Zephyr, an open-source Java-based instrument control and measurement software package. Zephyr was also used to acquire all data from the source-measure unit, the reference sensors, and the gas delivery system.

The response of the $WO_3$ nanoparticle network sensor to $H_2S$ exposure is shown in FIG. 1(c). FIG. 1(c) shows the current through the $WO_3$ nanoparticle sensor during a 100-second exposure to 50 ppm $H_2S$ at room temperature and at 300° C. The sensor was measured by applying a constant bias of 2.3 V across the source and drain electrodes. To heat the sensor, a voltage was applied to the heater leads such that the power delivered to the heater was 40 mW, which corresponded to 300° C. according to manufacturer calibration. At room temperature, the response to $H_2S$ was small (<<1 nA) with long response and recovery times (>>100 s). At 300° C., the sensor response was significantly higher (over 500 times larger) with a significantly faster response time ($t_{50}$=0.7 s; $t_{75}$=1.8 s).

The nanostructured nature of the sensing element has the added advantage of a higher surface area and could be thermally cycled using very little power and without suffering from fatigue. This allowed the sensor to be heated in short pulses, which decreased the overall power consumption of the device.

Figure 2:
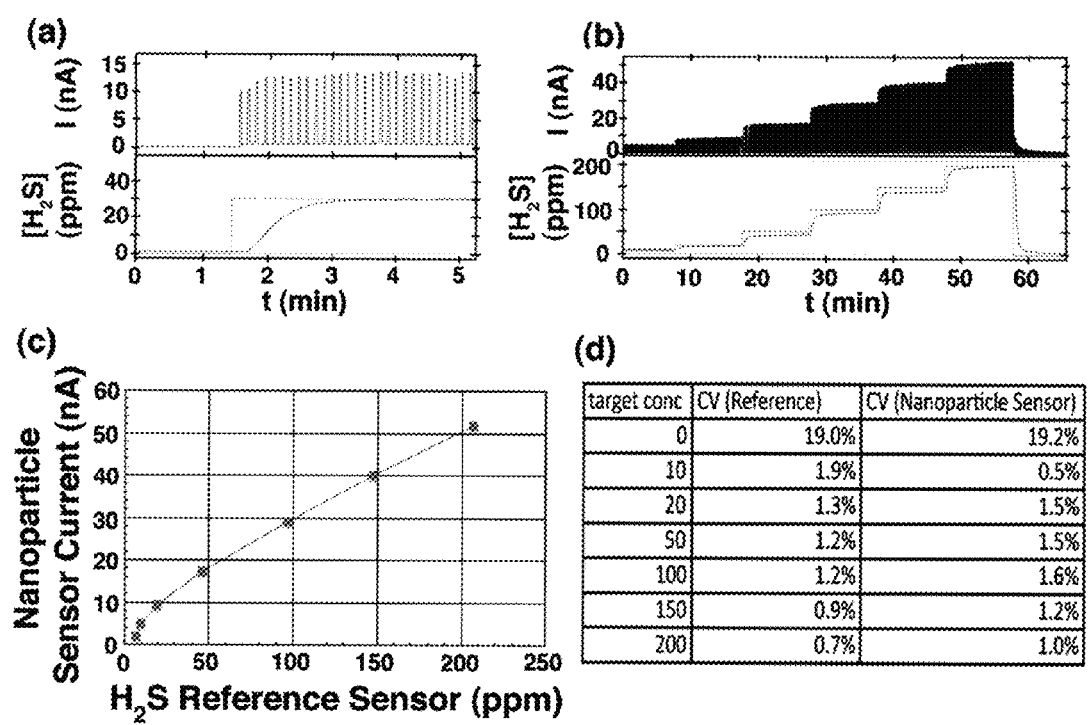
FIG. 2(a) shows a graph of nanoparticle sensor conductance while heat pulsing to 300° C. for 1 s every 6 s during exposure to 0 and 30 ppm of $H_2S$, according to embodiments of the present disclosure.
FIG. 2(b) shows a graph of sensor conductance during heatpulse operation when exposed to 10, 20, 50, 100, 150, 200, and 0 ppm $H_2S$, respectively.
FIG. 2(c) shows a graph of average sensor current while heated for each concentration set point versus average reference sensor reading for data shown in FIG. 2(b). Note: data during the first 3 min of the 10-min segment were not included in the analysis since the system had not reached steady state.
FIG. 2(d) shows a table showing the coefficient of variance (CV), defined as the standard deviation divided by the average, of the chemiluminescence reference sensor and the heated state current of the nanoparticle-based sensor for each of the concentration set points in FIG. 2(b).

FIG. 2 shows data from a $WO_3$ nanoparticle network sensor in the presence of different $H_2S$ concentrations while being heated for one second every six seconds. FIG. 2(a) shows the conductance versus time of the sensor as it was exposed to concentrations varying from 0 to 30 ppm. The conductance of the sensor in the heated state increased monotonically with $H_2S$ concentration. The response to 1 ppm $H_2S$ (time from 6000 s to 6600 s) was significantly larger than that of 0 ppm (from 7200 s to 7800 s), indicating the sensor had a very low limit of detection. The magnitude and speed of the sensor response while operating with heat pulses did not noticeably change. Sensors were heated tens of thousands of times during testing without showing response degradation.

FIG. 2 shows data from a $WO_3$ nanoparticle network sensor in the presence of different $H_2S$ concentrations while being heated for 1 s every 6 s. FIG. 2(a) shows the conductance versus time of the nanoparticle sensor while operating in heat-pulse mode as it was exposed to 0 and 30 ppm $H_2S$. The nanoparticle sensor responded as soon as the sensor was exposed to $H_2S$ (marked by the dotted line) and came to within 25% of its final value after the first heat pulse (6 s) and within 95% of its final value after only 4 pulses or about 25 s. The nanoparticle sensor responded faster than the reference sensor making the intrinsic response time of the sensor difficult to decouple from the system response time. This showed that the $WO_3$ nanoparticle sensor can be operated in heat pulse mode without significantly degrading the sensor response speed or magnitude. The average power consumed by the sensor operated in heat-pulse mode was less than 10 mW. The duration of the heat pulses have been decreased to 300 ms (data not shown) with similar results. The duration of this heat pulse can be decreased further since the calculated thermal response time of the sensor is only about 1 ms.

FIG. 2(b) shows the microheated $WO_3$ nanoparticle based $H_2S$ sensor conductance versus time operating in heatpulse mode during exposure to 10, 20, 50, 100, 150, 200, and 0 ppm $H_2S$, respectively. The sensor responded to changes in $H_2S$ concentration within a few heat pulses and with clearly distinguishable response magnitudes for different concentrations. The sensor response during concentration plateaus were not completely flat, due to a slow increase in the delivered $H_2S$ during the segment, which can be seen in the reference sensor data. FIG. 2(c) shows the average nanoparticle-based sensor current in the heated state during each concentration plateau (defined as the last 7 min of the 10-min segment) versus reference sensor reading during that plateau. The monotonic response curve showed that the nanoparticle-based sensor measured $H_2S$ in the entire range relevant to industrial and safety applications. The nanoparticle-based sensors also had a very low coefficient of variance (CV), i.e., the standard deviation divided by the mean, as shown in FIG. 2(d). The CV of the nanoparticle-base sensor was comparable to that of the more expensive and power hungry reference sensor (e.g., chemiluminescence sensor). The nanoparticle-based sensors were heated tens of thousands of times during testing without showing response degradation.

Figure 3:
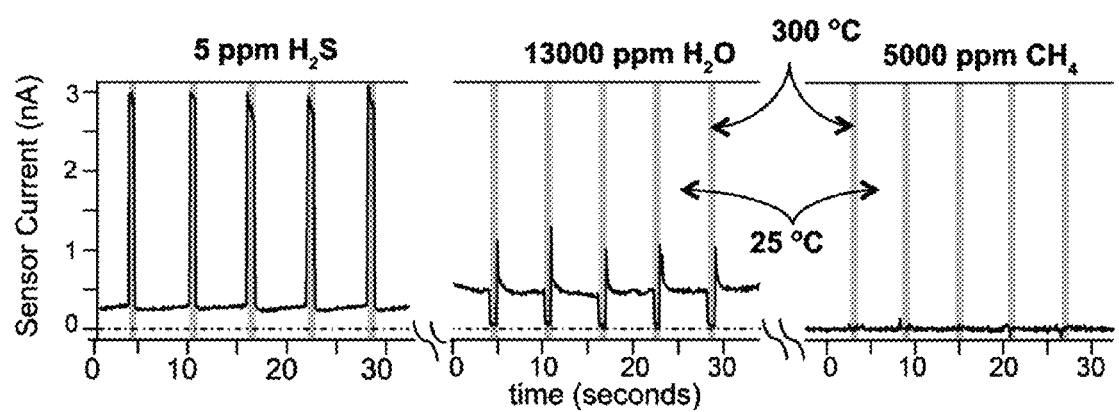
FIG. 3 shows graphs of sensor current vs. time for exposures to 5 ppm $H_2S$, 13,000 ppm $H_2O$, and 5000 ppm $CH_4$, according to embodiments of the present disclosure. Shaded areas indicate when the heater was on. Tick marks indicate 5-s intervals. During exposure to 13,000 ppm $H_2O$ (or 40% relative humidity at room temperature), sensor current during heating was low, indicating little cross-sensitivity to humidity. The sensor had little to no response to 0.5% $CH_4$.

The low-power sensor of the present disclosure was able to detect $H_2S$ as low as 1 ppm. In addition, the sensor was able to discriminate between the intended gas and interfering gases. To test the cross-sensitivity of the microheated $WO_3$ nanoparticle sensor, three gases expected to be seen during operation in the natural gas industry were chosen: methane—the major component of natural gas, hydrogen, and water vapor. FIG. 3 shows the conductance versus time during five 1-s heat pulses of a $WO_3$ nanoparticle sensor while being exposed to different environments: 5 ppm $H_2S$, 13,000 ppm $H_2O$ (or 40% relative humidity at room temperature), and 5000 ppm $CH_4$. The response to 5 ppm $H_2S$ is shown as a comparison to the sensor response to water and methane. The nanoparticle conductance during the unheated state was affected by the presence of the water. However, once the sensor was heated, the conductance dropped to virtually zero. In the unheated state, there was some adsorbed water on the surface of the sensor creating a network of water, thereby increasing the conductance slightly, possibly due to electrochemical reactions. When the sensor was heated, the water was driven off the surface and the conductance dropped to almost zero. Since the sensor reading was taken during the heated state, water had no direct effect on the sensor reading. The sensor conductance in the presence of methane showed no response. The microheated nanoparticle-based sensor did respond to hydrogen, and the sensitivity to hydrogen was about 0.03% of the sensitivity to hydrogen sulfide. There was little direct response to gases other than $H_2S$. The sensor was able to measure $H_2S$ in the presence of these other gases.

Without being limited to any particular theory, the sensing mechanism of the $WO_3$ nanoparticle network based $H_2S$ sensor is discussed below. For bulk $WO_3$-based $H_2S$ sensors, it was proposed that the $H_2S$ can either (1) reduce adsorbed oxygen, (2) donate a fraction of the sulfur lone pair electrons to the nanoparticle, or (3) exchange sulfur with oxygen in the nanoparticle. If the sensing mechanism were based on the reduction of surface adsorbed oxygen (mechanism 1), one would expect a strong response from hydrogen and a moderate response from methane. This was not observed for the sensor. Furthermore, the speed of response was much faster than that would be expected from anion exchange within the nanoparticle lattice (mechanism 3).

The underlying sensing mechanism for this $WO_3$ nanoparticle-based $H_2S$ sensor may be due to electron donation from the $H_2S$ to the $WO_3$ nanoparticles (mechanism 2 above). When $H_2S$ donated electrons to the $WO_3$, impurity states were filled, increasing the Fermi energy. With higher concentrations of $H_2S$ more impurity states were filled, and the Fermi energy correspondingly increased. Since tungsten oxide is an n-type semiconductor, as the Fermi energy increased, the barrier height for electrons to be excited into the conduction band decreased, and, therefore, the number of thermally excited carriers increased. This caused the resistance of the nanoparticles and therefore the network as a whole to decrease.

Water does not affect the sensor the way hydrogen sulfide does even though the two molecules have a similar structure. This is because oxygen is much more electronegative than sulfur, so the lone pairs on oxygen in water are more tightly bound to the molecule than the lone pairs on sulfur in hydrogen sulfide. Therefore, when hydrogen sulfide adsorbs on the surface of a nanoparticle, it donates some fraction of its electrons to the nanoparticle, whereas water does not.

To determine whether the proposed sensing mechanism was consistent with the electrical transport data, the conductance of the nanoparticle network at room temperature was compared to that at 300° C. for each $H_2S$ concentration. The conductivity σ of the nanoparticle is given by σ=neµ, where n is the number of charge carriers, e is the elementary charge, and µ is the mobility of the charge carriers. If it is assumed that the nanoparticles are in ohmic contact with one another and the electrical leads and that the mobility is constant with temperature, then the conductance of the nanoparticle network would be proportional to the number of charge carriers n. Since the conductance of the network was higher in the heated state than in the non-heated state for all $H_2S$ concentrations, the carriers were thermally activated. The charge carrier concentration n is approximately proportional to $e^{(E_f-E_c)/k_bT}$, where $E_f$ is the Fermi energy, $E_c$ is the conduction band edge, $k_b$ is the Boltzmann constant, and T is the absolute temperature. Therefore, from the ratio of the nanoparticle network conductance at room temperature and at 300° C., the difference between $E_c$ and $E_f$ can be determined for each $H_2S$ concentration. The excitation barrier decreased with increasing $H_2S$ concentration (data not shown), which was consistent with electrons filling defect states causing the Fermi level to increase.

In summary, microheated nanoparticle network gas sensors were tested that were fast, low-power, sensitive, and selective. The $WO_3$-nanoparticle-based hydrogen sulfide gas sensor had a response time of a few seconds, low or no direct sensitivity to water, methane, or hydrogen, consumed less than 10 mW of power and were fabricated at low cost in large quantities. The sensing mechanism was believed to be related to electron donation from the $H_2S$ to the $WO_3$, which caused the Fermi energy to increase, creating more charge carriers in the nanoparticle and, thereby, decreasing the sensor resistance. While the experiments were directed to hydrogen sulfide sensing, this sensor platform can be used for many other gases of interest by tailoring the sensing nanomaterials to the analyte of interest.

Example 2

Low Power Multifunctional Gas Sensor Arrays

Introduction

Experiments were performed using sensors of the present disclosure to: (1) reduce power consumption of the microheater; (2) reduce the gap between the electrodes contacting the sensing layer; and (3) provide an array of sensors on one device.

A sensing chip was designed and fabricated with lower power consumption (~3 mW), quicker thermal response time (~25 µs), smaller sensing gap (~2 µm), and multiple (72) microheater on one chip. In addition, the sensing system added multiplexer circuits to enable measurement of dozens of microheater-based sensors. Each of the dozens of microheaters can be functionalized with different sensing layers to enable multi-gas characterization of the environment.

Design of the Microheaters

Figure 4:
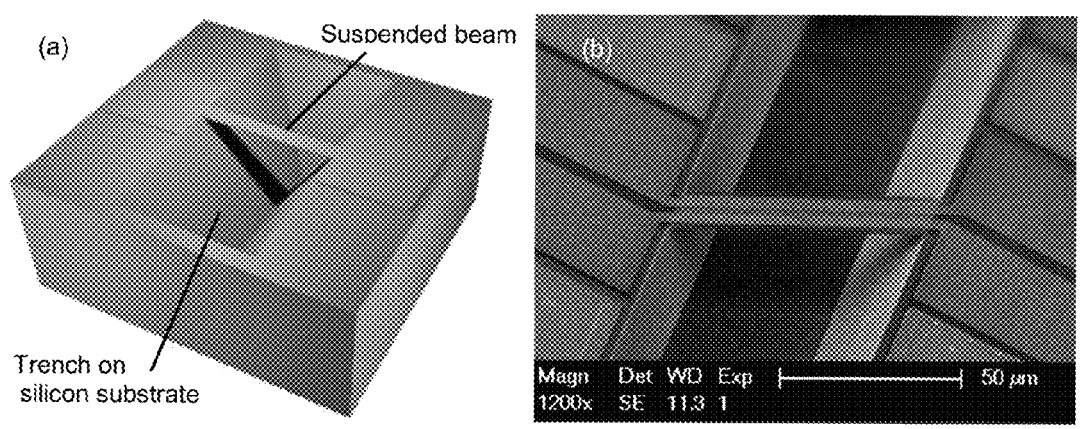
FIG. 4(a) shows a schematic drawing of a suspended microheater, according to embodiments of the present disclosure.
FIG. 4(b) shows an image of a fabricated microheater.

The heater was joule heated with electric current flow. Polysilicon was chosen as the resistive heating material for its compatibility with micromachining processes and its high resistance to electromigration. To reduce the power consumption, the heater was designed to be suspended (FIG. 4). To optimize the heater performance, an equation on the heater power consumption was derived.

Neglecting radiation, two heat loss channels contributed to the total power consumption of the microheaters: (1) heat conduction through the beam to the substrate; and (2) heat conduction through air to the substrate and environment (convection was negligible at this scale).

The heat resistance of the beam can be estimated as:

$$R_{thermal} = \frac{L}{8kwt} \quad (1)$$

where L is the length of the beam, k is the thermal conductivity of the material, w is the width of the beam, and t is the thickness of the beam. The rough estimation assumed a linear temperature distribution from the root of the beam at room temperature to the center of the beam where the maximum temperature was reached. The power loss through the beam was therefore:

$$P_{beam} = \frac{\Delta T}{R_{thermal}} = \frac{8\Delta Tkwt}{L} \quad (2)$$

where $\Delta T$ is the maximum temperature of the beam. In the following derivation all the temperatures were relative to the environment temperature for convenience.

To estimate the heat loss through air, the temperature profile around the microheater is identified. Because the heater was long and slim (t, w<<L), the heat loss was estimated as two-dimensional heat conduction in the planes perpendicular to the length direction of the beam. The beam was treated as a cylinder with diameter w, length L, and temperature $\Delta T$. The temperature profiles in the planes perpendicular to the length direction of the beam by solving the two-dimensional Poison equation is therefore:

$$T = \frac{\ln(D_\infty/2) - \ln r}{\ln D_\infty - \ln w} \Delta T \quad (3)$$

where $D_\infty$ is the diameter where the temperature approaches environment temperature, and r is the radial coordinate. The heat conduction through air is therefore:

$$P_{air} = \oiint k_{air} \frac{\partial T}{\partial r} dA = k_{air} \frac{\partial T}{\partial r}\bigg|_{r=D/2} \frac{\pi w L}{2} \quad (4)$$

where $k_{air}$ is the thermal conductivity of the air, and the factor 2 comes from the fact that the beam temperature is not uniform but with a maximum at its center. For the same reason $D_\infty$ can be approximated as L. Substitute Equation (3) into (4):

$$P_{air} = \frac{\pi k_{air} L}{\ln(L/w)} \Delta T \quad (5)$$

and combine Equation (2) and (5), which gives the total power consumption:

$$P = P_{air} + P_{beam} = \Delta T \left( \frac{\pi k_{air} L}{\ln(L/w)} + \frac{8kwt}{L} \right) \quad (6)$$

Figure 5:
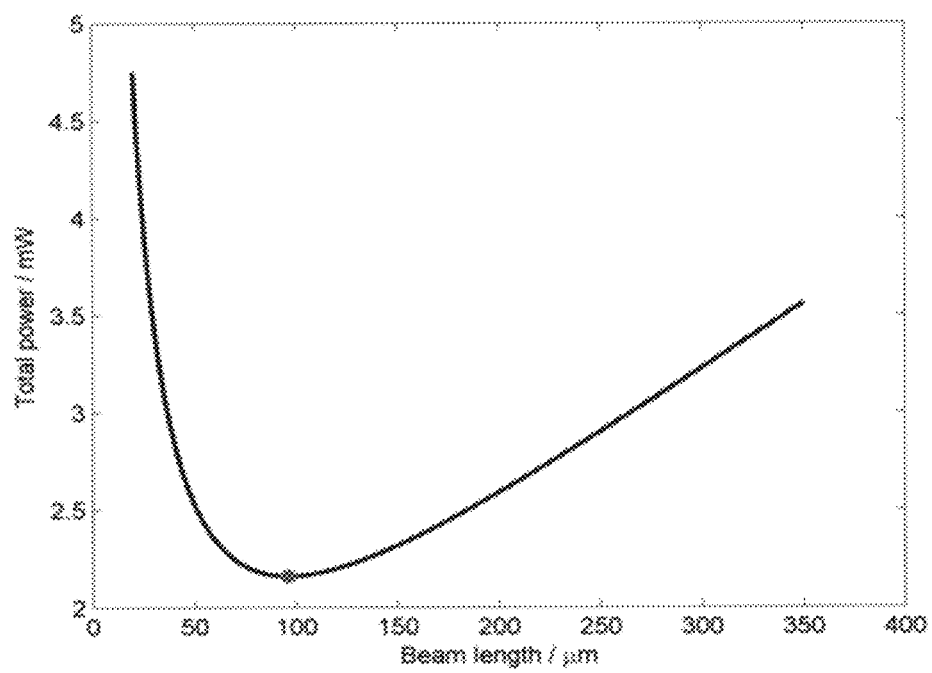
FIG. 5 shows a graph of total power (mW) vs. heater beam length (μm) for the optimization of the heater beam length for minimal power consumption, according to embodiments of the present disclosure.

The beam length can therefore be optimized for the lowest power consumption (FIG. 5), when the other parameters are fixed due to fabrication considerations (i.e., t=200 nm, due to film stress and mechanical strength consideration; and w=4 µm, due to lithography precision). It was determined that the optimum beam length was ~100 µm and the power consumption was ~2 mW. It was observed that shorter beam resulted in larger heat loss through beam conduction, while longer beam resulted in larger heat loss through air.

Figure 6:
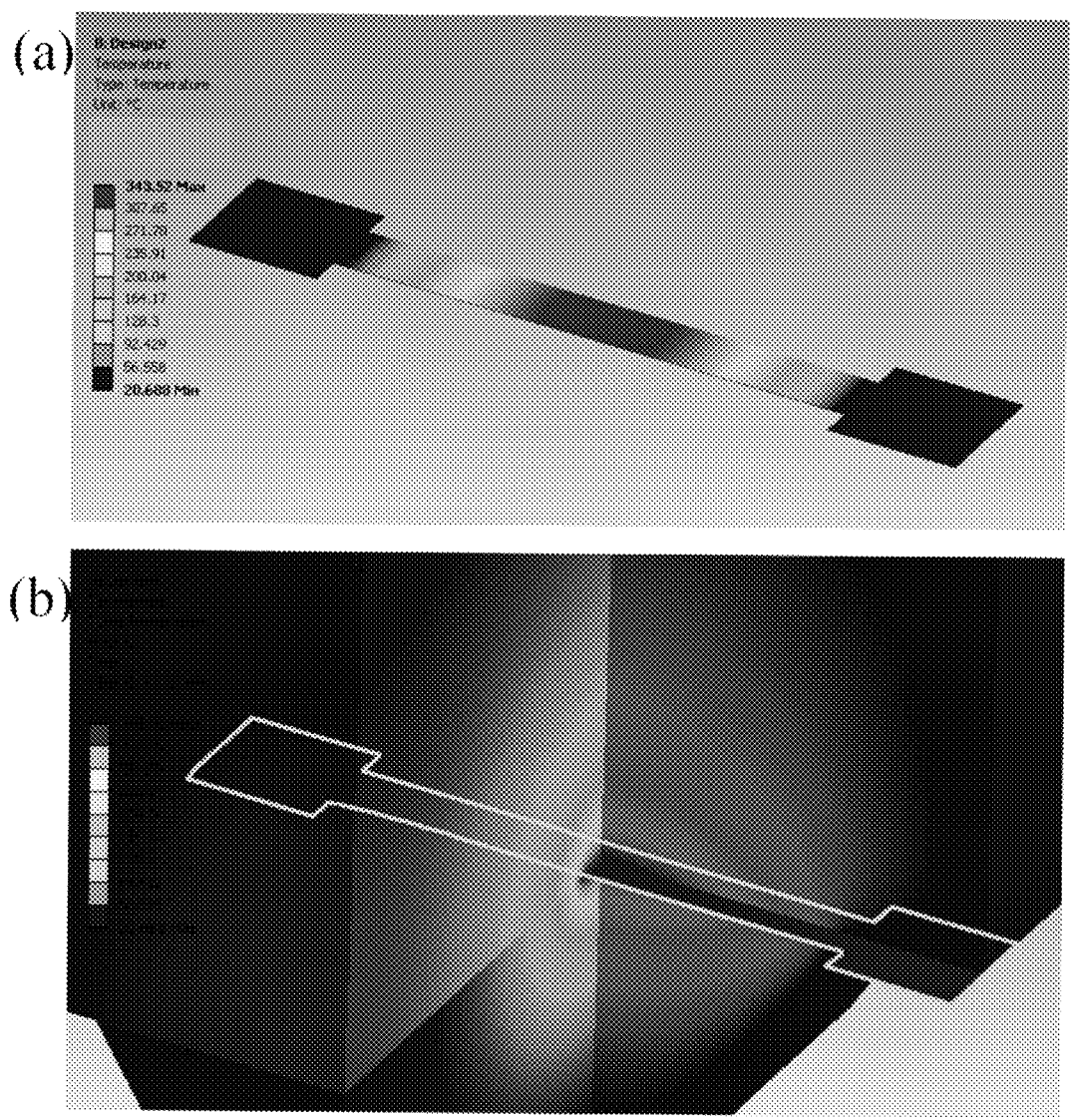
FIG. 6(a) shows temperature distribution of the beam of a microheater.
FIG. 6(b) shows the temperature distribution of the air around the beam, according to embodiments of the present disclosure.

To verify this analytical calculation, a simulation was performed in ANSYS® (FIG. 6) with the optimized parameters. The simulation gave a total power of 2.5 mW, with 1.2 mW lost through beam conduction, and 1.3 mW lost through air conduction, which was in good agreement with the analytical analysis. Various beam dimensions and designs were designed and fabricated around this optimized value.

Sensor Design

For gas sensing applications, two components were also included in the sensor: the sensing electrodes for contacting the gas sensing layer and the temperature sensor. In addition, the polysilicon microheater was passivated by an insulating dielectric material. Silicon-rich nitride was chosen as the passivation layer material because it can also serve as the etching mask for the final device-releasing step. The gap between the two sensing electrodes should be small in the case of nanoparticle based sensing layer. The gap was therefore designed to be 2 µm or 4 µm. Two mechanisms were used for temperature sensing: resistive temperature detector (RTD) and thermal couple (TC). The resistivity of platinum (Pt) has a large (temperature coefficient 0.003729 at room temperature) and linear temperature response over a wide temperature range, therefore Pt was used as the RTD material. To reduce the fabrication complexity, Pt was also used as one electrode material of the TC. The other electrode was made from gold (Au), which was resistant to silicon etching during the fabrication process.

Figure 7:
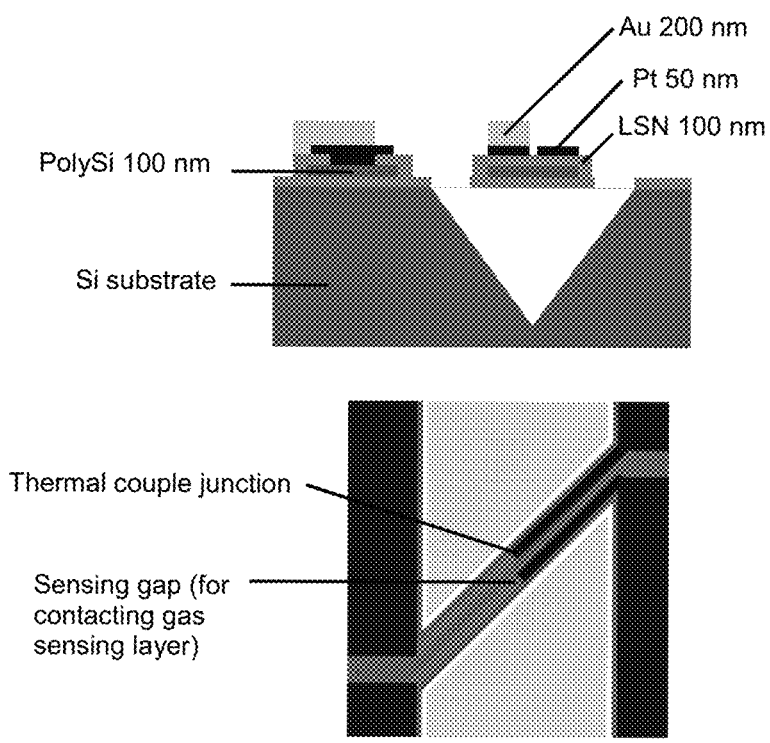
FIG. 7 shows a schematic drawing of a sensor (profile and top view), according to embodiments of the present disclosure.

Several parameters were varied through the different sensor designs. The beam width was either 4 µm, 8 µm, 10 µm, or 16 µm; the beam length was either 56 µm, 80 µm or 120 µm; the temperature sensor was either average Pt RTD, Pt RTD at the heated region contacted by the Au electrodes, or a Pt—Au TC; and the gas sensing electrode gap was either 2 µm or 4 µm. 27 different variations of the sensor were designed. FIG. 7 shows one of the sensors.

Fabrication of the Microsensor Array

Figure 8:
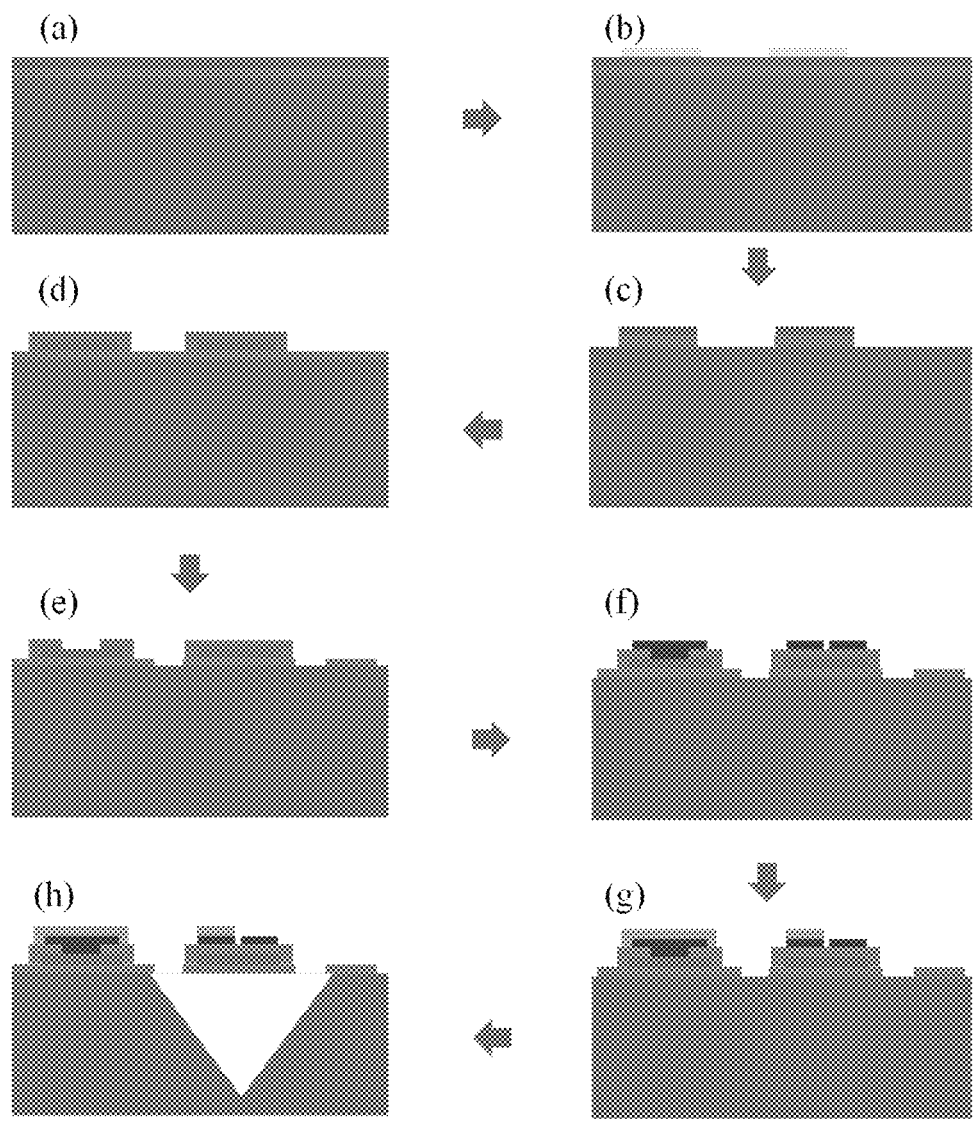
FIGS. 8(a)-(h) show a fabrication process flow for the microsensor array, according to embodiments of the present disclosure.

The fabrication of the microsensors was a 4-mask surface micromachining process followed by a final KOH etch to release the suspended beam structure. 72 microheaters were integrated on one sensor chip with an area of 3.2 mm×3.0 mm. The process is illustrated in FIG. 8. The silicon substrate was first deposited with 100 nm silicon-rich low-stress nitride (LSN), followed by 100 nm undoped polysilicon and 2 µm boron doped silicon dioxide. The wafers were heated to 1050° C. for film stress release and dopant diffusion into the polysilicon layer. The oxide layer was then removed in buffered hydrogen fluoride (BHF) etch bath (FIG. 8(a)). 1-µm Fujifilm® OiR 897 photoresist was spun on the substrate and patterned with photolithography (mask 1, FIG. 8(b)). The polysilicon layer and the LSN layer were sequentially etched in a plasma etcher, where the photoresist served as the etching mask. The photoresist was stripped off with acetone and the wafers were cleaned in piranha solution (FIG. 8(c)). Another 100-nm-thick LSN layer was deposited (FIG. 8(d)) and patterned with similar photolithography-etching-cleaning technique (mask 2, FIG. 8(e)). Another photoresist was spun on and patterned (mask 3), and 10/60 nm thick chromium/platinum layer was e-beam evaporated onto the substrate. The chromium layer was used as an adhesion layer between the substrate and platinum. The metal layer was patterned following a lift-off process in acetone in an ultrasonic bath (FIG. 8(f)). The wafers were annealed in nitrogen environment at 350° C. for 1 hour to release Pt film stress. After that, a similar photolithography-evaporation-lift off process was carried out to deposit another patterned layer of 10/100 nm thick chromium/gold (mask 4, FIG. 8(g)). Finally, the wafers were diced into individual chips and released in a KOH etching bath at 80° C. (FIG. 8(h)).

Characterization of the Microheaters

Figure 9:
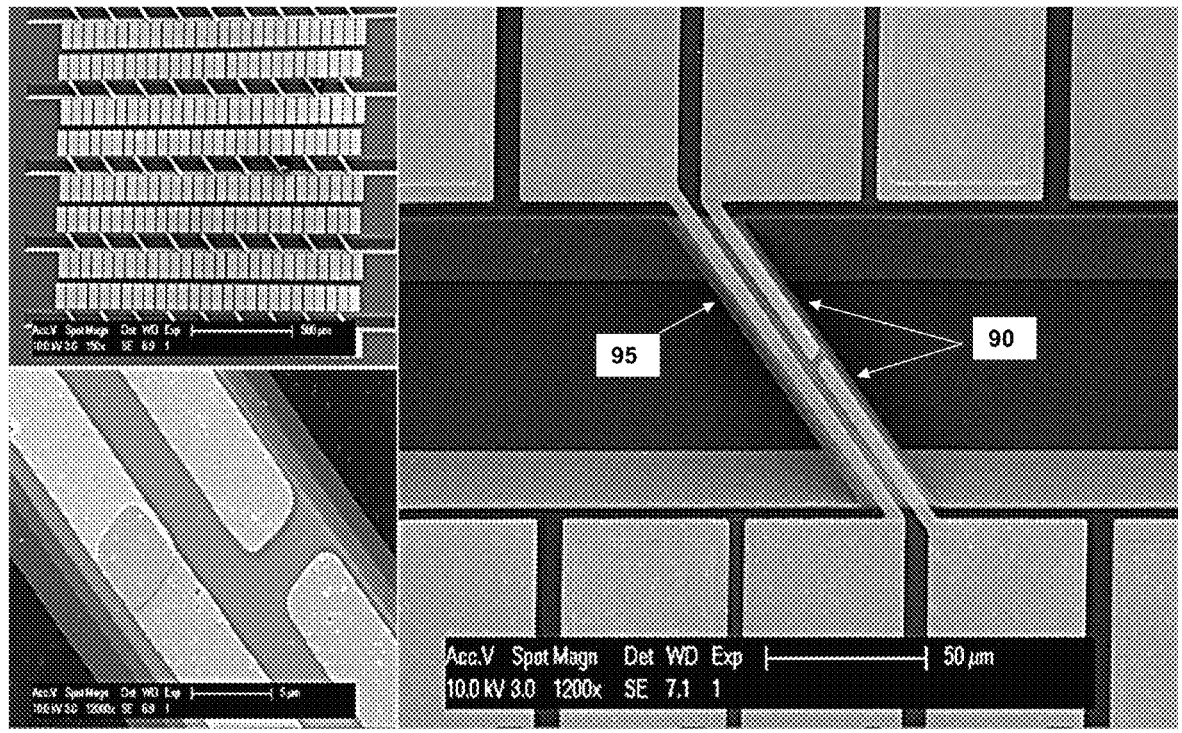
FIG. 9 shows SEM images of a microsensor array according to embodiments of the present disclosure.

After release in KOH bath, the microsensor array was first characterized by SEM (FIG. 9). The beams were suspended over trenches of approximately 20 µm in depth. The magnified view shows a beam with a sensing electrode pair and a thermal couple (Pt—Au) integrated. FIG. 9 shows the electrodes 90 of the gas sensing element and the thin-film heating element 95. Also shown in FIG. 9 is the gap between the electrodes of the gas sensing element (see also FIG. 14).

Figure 10:
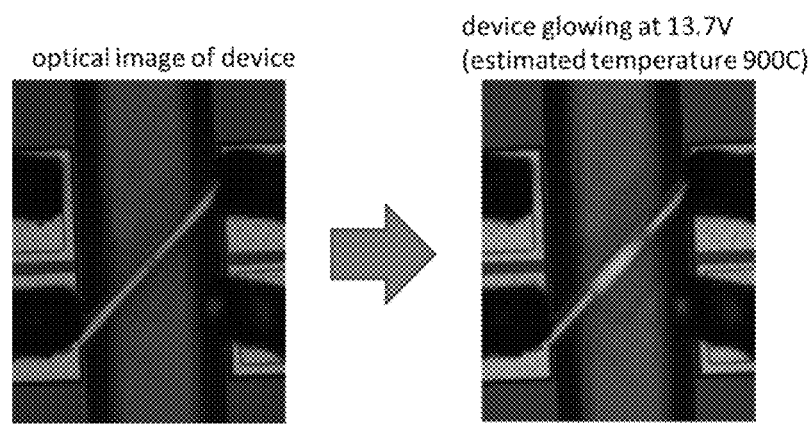
FIG. 10 shows images of a heater high temperature test, according to embodiments of the present disclosure.

The gas sensor chip was then placed inside a ceramic package and was wire-bonded to make electrical connections. A device absolute-maximum-rating test was done on a heater with the following parameters: beam width: 10 µm; length: 110 µm; trench width: 74 µm (FIG. 10). The heater was driven to glowing temperature at an estimated 900° C. with 13.7 V. The electrical current was 2.5 mA. The heater failed when the voltage reached 14 V. This test demonstrated that the heater temperature range was sufficiently large to cover the sensor operating temperature of 300° C.

Figure 11:
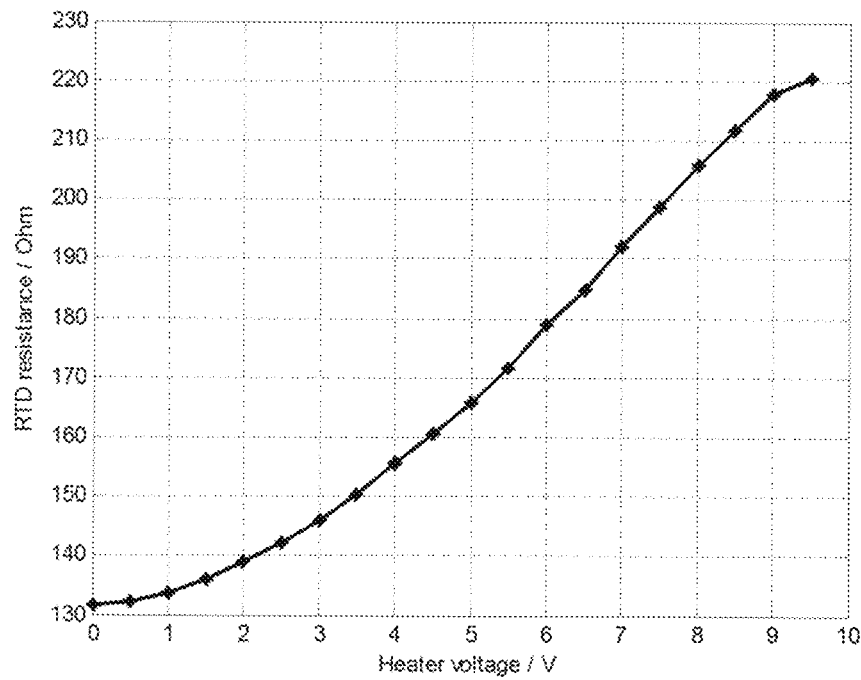
FIG. 11 shows a graph of RTD resistance vs. voltage applied on the heater, according to embodiments of the present disclosure.
Figure 12:
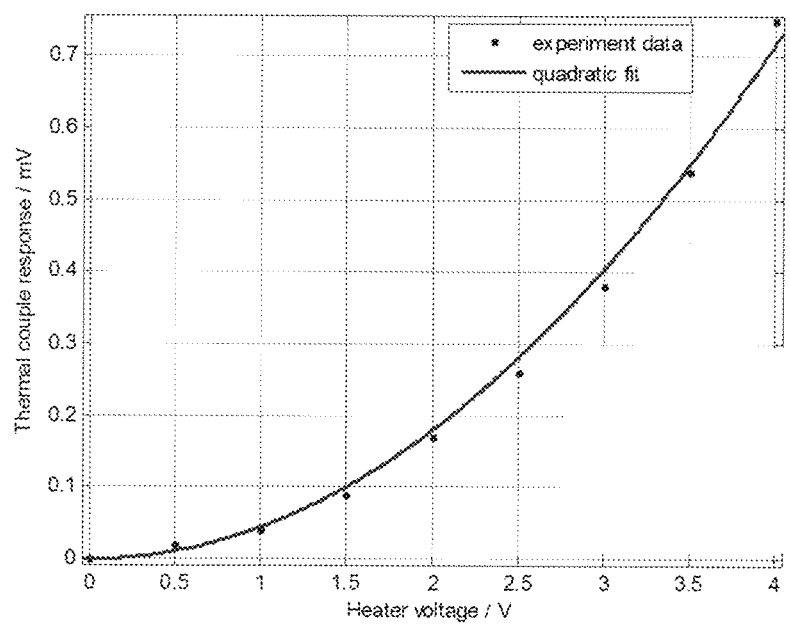
FIG. 12 shows a graph of thermal couple response (mV) vs. heater voltage (V) for a microheater, according to embodiments of the present disclosure.

Tests were performed on the resistive temperature detector (FIG. 11). It was found that at 9.5 V, the heater started to glow at an estimated temperature of 700° C. According to the RTD reading, the heater temperature reached 300° C. with ~5V supply voltage and ~3 mW power consumption. The performance of the integrated Au—Pt thermal couple was also tested (FIG. 12).

Response should be proportional to the square of heating voltage if heater resistance remains constant (From $P=V^2/R$, $\Delta T \propto P$, and $V_{TC} \propto \Delta T$, we have $V_{TC} \propto V^2$).

$H_2S$ Sensing Results

The low power microheated sensor was tested using networks of $WO_3$ nanoparticles for $H_2S$ detection. By using a small and low power microheater in the sensor array, $H_2S$ was detected down to 1 ppm, while the peak power consumption was 1.5 mW and the average power consumption was 250 µW. FIG. 13 shows a graph of the current through the $WO_3$ nanoparticle network while operating in a low duty-cycle heat-pulse mode. As the sensor was heated, the current increased due to the semiconducting nature of $WO_3$. The current during the heated phase increased with increasing $H_2S$ concentration.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A gas sensor comprising:
   a gas sensing element comprising metal oxide nanoparticles and a first elongated electrode and a second elongated electrode; and
   a substantially linear elongated thin-film heating element;

wherein the first elongated electrode and the second elongated electrode are parallel to the elongated thin-film heating element.

2. The gas sensor of claim 1, wherein the metal oxide nanoparticles are disposed between the first elongated electrode and the second elongated electrode.

3. The gas sensor of claim 1, wherein the metal oxide nanoparticles comprise tungsten oxide nanoparticles and the gas sensor is configured to detect hydrogen sulfide.

4. The gas sensor of claim 3, wherein the metal oxide nanoparticles have an average diameter of 100 nm or less.

5. The gas sensor of claim 1, wherein the thin-film heating element comprises polysilicon.

6. The gas sensor of claim 1, further comprising an insulation layer between the gas sensing element and the thin-film heating element.

7. The gas sensor of claim 6, wherein the insulation layer comprises silicon nitride.

8. The gas sensor of claim 1, wherein the gas sensor is configured to have a thermal efficiency ranging from 30° C./mW to 200° C./mW.

9. The gas sensor of claim 1, wherein the gas sensor is configured to have a limit of detection of 1 ppm or less.

10. The gas sensor of claim 1, wherein the metal oxide nanoparticles comprise groupings of the metal oxide nanoparticles that do not substantially contact surrounding groupings of the metal oxide nanoparticles but are interconnected by one or more bridges of the metal oxide nanoparticles.

11. A gas sensor system comprising:
one or more gas sensors, wherein each gas sensor comprises:
a gas sensing element comprising metal oxide nanoparticles and a first elongated electrode and a second elongated electrode; and
a substantially linear elongated thin-film heating element;
wherein the first elongated electrode and the second elongated electrode are parallel to the elongated thin-film element.

12. The gas sensor system of claim 11, wherein the gas sensor system comprises an array of gas sensors.

13. The gas sensor system of claim 12, wherein the array comprises 6 or more gas sensors.

14. The gas sensor system of claim 12, wherein the array has a length of 3 mm or less and a width of 3 mm or less.

15. The gas sensor system of claim 11, further comprising a controller configured to repeatedly activate and deactivate the thin-film heating element over a period of time.

16. The gas sensor system of claim 15, wherein the controller is configured to activate the thin-film heating element with a duty cycle of 20% or less.

17. The gas sensor system of claim 15, wherein the controller is configured to activate the thin-film heating element with a frequency of 0.1 Hz or more.

18. A method of detecting whether an analyte is present in a gaseous sample, the method comprising:
contacting a gaseous sample to a gas sensor to produce a signal, the gas sensor comprising:
a gas sensing element comprising metal oxide nanoparticles and a first elongated electrode and a second elongated electrode; and
a substantially linear elongated thin-film heating element;
wherein the first elongated electrode and the second elongated electrode are parallel to the elongated thin-film element; and
analyzing the signal to determine whether the analyte is present in the gaseous sample.

19. The method of claim 18, further comprising heating the gas sensing element with the thin-film heating element during the contacting.

20. The method of claim 19, wherein the heating comprises repeatedly activating and deactivating the thin-film heating element over a period of time.

21. The method of claim 18, further comprising determining the concentration of the analyte in the gaseous sample based on the signal.

22. The method of claim 21, further comprising activating an alarm if the concentration of the analyte is greater than a threshold value.

* * * * *